United States Patent
Harada et al.

(10) Patent No.: US 7,538,117 B2
(45) Date of Patent: May 26, 2009

(54) CRYSTALLINE AND AMORPHOUS PYRIMIDINE COMPOUNDS AND PROCESSES FOR PREPARING PYRIMIDINE COMPOUNDS

(75) Inventors: Hitoshi Harada, Tsukuba (JP); Hiroyuki Chiba, Kamisu (JP); Yuki Komatsu, Kamisu (JP); Susumu Inoue, Kamisu (JP); Naoki Ozeki, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 296 days.

(21) Appl. No.: 11/378,307

(22) Filed: Mar. 20, 2006

(65) Prior Publication Data

US 2007/0078151 A1  Apr. 5, 2007

Related U.S. Application Data

(60) Provisional application No. 60/663,580, filed on Mar. 21, 2005.

(51) Int. Cl.
  *A01N 43/54* (2006.01)
  *A61K 31/505* (2006.01)
(52) U.S. Cl. .................................................. 514/275
(58) Field of Classification Search .................. None
  See application file for complete search history.

(56) References Cited

U.S. PATENT DOCUMENTS

2005/0004149 A1  1/2005  Harada et al.

FOREIGN PATENT DOCUMENTS

| EP | 1439175 A1 | 7/2004 |
| WO | WO03/035639 | * 1/2003 |
| WO | WO-03/035639 A1 | 5/2003 |
| WO | WO-2004/016605 A1 | 2/2004 |

OTHER PUBLICATIONS

Selvamurugan et al., Tetrahedron, vol. 57, pp. 6065-6069, (2001).
Fischer et al., J. Org. Chem., vol. 52, pp. 564-569, (1987).

* cited by examiner

*Primary Examiner*—James O. Wilson
*Assistant Examiner*—Jeffrey H Murray
(74) *Attorney, Agent, or Firm*—Birch, Stewart, Kolasch & Birch, LLP

(57) ABSTRACT

Crystals of 5-[2-amino-4-(2-furyl)pyrimidin-5-yl]-1-methylpyridin-2(1H)-one having a diffraction peak at a diffraction angle (2θ±0.2°) of 9.7° and/or 21.9° in a powder X-ray diffraction are suitable for an active ingredient of a preventing and therapeutic agent for diseases such as constipation. Crystals of 5-[2-amino-4-(2-furyl)pyrimidin-5-yl]-1-methylpyridin-2(1H)-one hydrate and amorphous 5-[2-amino-4-(2-furyl)pyrimidin-5-yl]-1-methylpyridin-2(1H)-one hydrate are also suitable for an active ingredient of a preventing and therapeutic agent for diseases such as constipation.

3 Claims, 17 Drawing Sheets

CRYSTALLINE AND AMORPHOUS PYRIMIDINE COMPOUNDS AND PROCESSES FOR PREPARING PYRIMIDINE COMPOUNDS

CROSS-REFERENCE TO RELATED APPLICATIONS

This application claims priority to a provisional application Ser. No. 60/663,580 filed on Mar. 21, 2005 by the same Applicant, which is hereby incorporated by reference in its entirety.

BACKGROUND OF THE INVENTION

1. Field of the Invention

The present invention relates to crystalline and amorphous pyrimidine compounds, and processes for preparing the same. More particularly, the present invention relates to crystals (the crystal form C) of 5-[2-amino-4-(2-furyl)pyrimidin-5-yl]-1-methylpyridin-2(1H)-one, a compound effective for prevention and treatment for various diseases such as constipation, and processes for preparing the same; crystals of 5-[2-amino-4-(2-furyl)pyrimidin-5-yl]-1-methylpyridin-2(1H)-one hydrate and processes for preparing the same; and amorphous 5-[2-amino-4-(2-furyl)pyrimidin-5-yl]-1-methylpyridin-2(1H)-one and processes for preparing the same. The present invention relates also to processes for preparing pyrimidine compounds such as 5-[2-amino-4-(2-furyl)pyrimidin-5-yl]-1-methylpyridin-2(1H)-one and intermediates thereof.

2. Related Background of the Invention

5-[2-Amino-4-(2-furyl)pyrimidin-5-yl]-1-methylpyridin-2(1H)-one is a compound having adenosine receptor antagonism and being effective for prevention and treatment for various diseases such as constipation (see patent document 1). Patent document 1, Example 16 discloses 5-[2-amino-4-(2-furyl)pyrimidin-5-yl]-1-methylpyridin-2(1H)-one was obtained as crystals.

The process for preparing 5-[2-amino-4-(2-furyl)pyrimidin-5-yl]-1-methylpyridin-2(1H)-one disclosed in patent document 1 is, as shown in the reaction scheme below, a method of allowing 2-(6-chloro-3-pyridyl)-3-dimethylamino-1-(2-furyl)-2-propene-1-one to react with guanidine to afford 5-(6-chloro-3-pyridyl)-4-(2-furyl)-2-pyrimidinylamine, oxidizing this to afford 5-[2-amino-4-(2-furyl)-5-pyrimidinyl]-1,2-dihydro-2-pyridinone, and then methylating this.

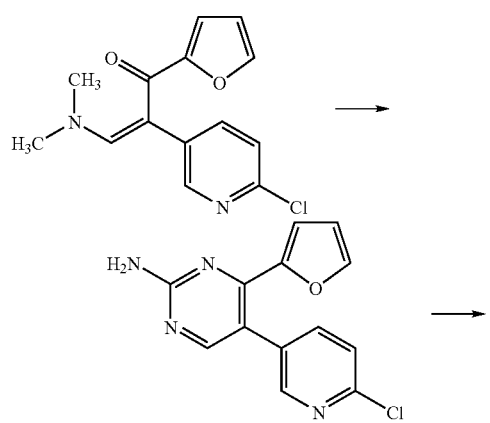

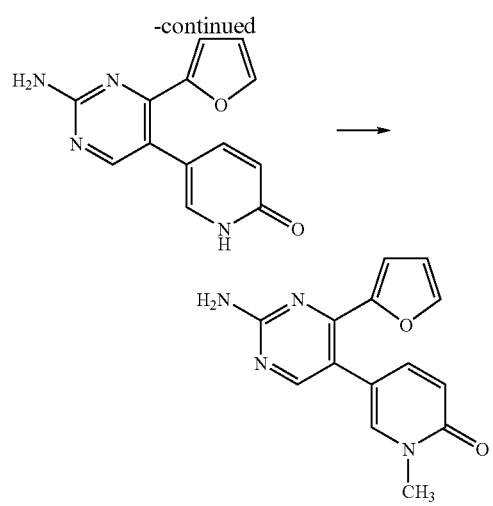

Also is disclosed in patent document 1, a method of acidizing 5-(6-benzyloxy-3-pyridyl)-4-(2-furyl)-2-pyrimidinylamine to afford 5-[2-amino-4-(2-furyl)-5-pyrimidinyl]-1,2-dihydro-2-pyridinone.

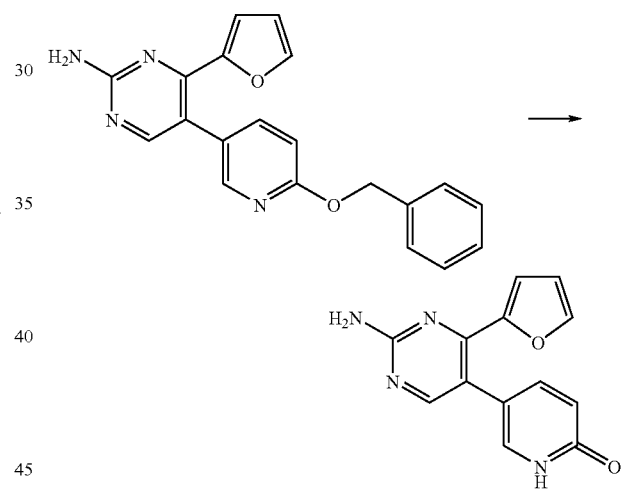

Furthermore, the following reaction is described as general production method D in patent document 1.

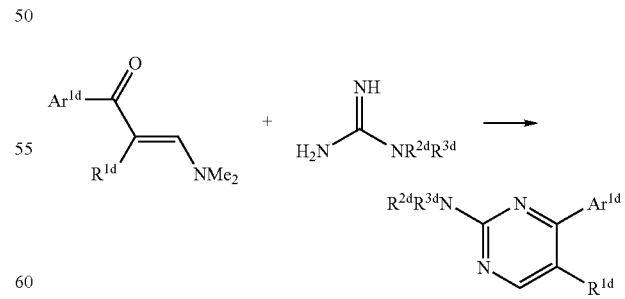

In the above formula, $R^{1d}$ represents a C6-14 aromatic hydrocarbon ring group, a 5- to 14-membered aromatic heterocyclic group, etc., but the reaction in which $R^{1d}$ is N-alkyl pyridone is not specifically disclosed.

Patent Document 1: WO 03/035639

SUMMARY OF THE INVENTION

The active ingredient of a drug must be stably supplied as a product of consistent quality. Therefore, when the active ingredient of a drug is obtained as a crystalline substance, it preferably consists of a homogenous crystal form with suitable physical properties such as good solubility. Therefore an object of the present invention is to provide crystals of 5-[2-amino-4-(2-furyl)pyrimidin-5-yl]-1-methylpyridin-2(1H)-one having suitable physical properties.

According to the process for preparing pyrimidine compounds such as 5-[2-amino-4-(2-furyl)pyrimidin-5-yl]-1-methylpyridin-2(1H)-one disclosed in patent document 1, the two steps are necessary in order to obtain N-alkyl pyridone, the final product, from a pyridine form: (1) oxidation from pyridine to pyridone; and (2) N-alkylation of pyridone ring. In general, preparing process having fewer steps is industrially advantageous. Furthermore, an alkyl halide and a base are necessary for N-alkylation of pyridone ring. Alkyl halides are easily degradable in the presence of a base, consequently are required more than one equivalent with respect to starting materials, but it is requested that the amount of alkyl halides used should be reduced due to their toxicity. Therefore, another object of the present invention is to provide a process for preparing pyrimidine compounds such as 5-[2-amino-4-(2-furyl)pyrimidin-5-yl]-l-methylpyridin-2(1H)-one having an advantage of fewer steps and less amount of alkyl halides used.

As a result of much avid research, the present inventors have discovered crystalline and amorphous 5-[2-amino-4-(2-furyl)pyrimidin-5-yl]-1-methylpyridin-2(1H)-one which are superior in solubility than the crystals disclosed in patent document 1 (hereinafter referred to as the crystal form B), and have succeeded in completing this invention.

Specifically, the present invention provides the following [1] to [9].

[1] A crystal of 5-[2-amino-4-(2-furyl)pyrimidin-5-yl]-1-methylpyridin-2(1H)-one having a diffraction peak at a diffraction angle (2θ±0.2°) of 9.7° and/or 21.9° in a powder X-ray diffraction.
[2] A crystal of 5-[2-amino-4-(2-furyl)pyrimidin-5-yl]-1-methylpyridin-2(1H)-one having a peak at a chemical shift of approximately 134.9 ppm and/or approximately 146.3 ppm in a $^{13}$C solid state nuclear magnetic resonance spectrum (hereinafter referred to as $^{13}$C solid state NMR spectrum).
[3] A process for preparing a crystal according to [1] or [2], by heating and drying amorphous 5-[2-amino-4-(2-furyl)pyrimidin-5-yl]-1-methylpyridin-2(1H)-one at a high-temperature region.
[4] A crystal of 5-[2-amino-4-(2-furyl)pyrimidin-5-yl]-1-methylpyridin-2(1H)-one hydrate.
[5] A crystal of 5-[2-amino-4-(2-furyl)pyrimidin-5-yl]-1-methylpyridin-2(1H)-one monohydrate.
[6] A crystal of 5-[2-amino-4-(2-furyl)pyrimidin-5-yl]-1-methylpyridin-2(1H)-one hydrate having a diffraction peak at a diffraction angle (2θ±0.2°) of 8.8° in a powder X-ray diffraction.
[7] A process for preparing a crystal according to any one of [4] to [6], by humidifying a crystal according to [1] or [2].
[8] Amorphous 5-[2-amino-4-(2-furyl)pyrimidin-5-yl]-1-methylpyridin-2(1H)-one hydrate.
[9] A process for preparing an amorphous compound according to [8], by lyophilizing a solution of 5-[2-amino-4-(2-furyl)pyrimidin-5-yl]-1-methylpyridin-2(1H)-one.

The present inventors have discovered a process for preparing pyrimidine compounds such as 5-[2-amino-4-(2-furyl)pyrimidin-5-yl]-1-methylpyridin-2(1H)-one, having fewer steps and less amount of alkyl halides used than that disclosed in patent document 1, and have succeeded in completing this invention.

Specifically, the present invention provides the following [10] to [22].

[10] A process for preparing a compound (I), a salt or a hydrate of the foregoing

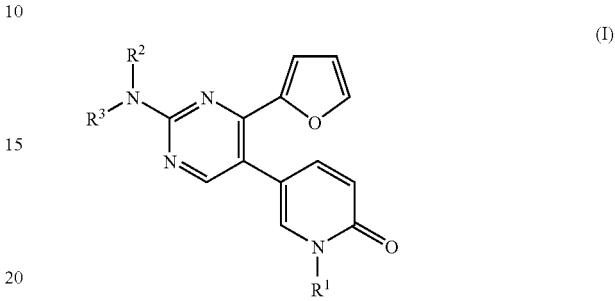

wherein $R^1$ represents C1-6 alkyl and $R^2$ and $R^3$ independently represent hydrogen or C1-6 alkyl, by allowing a compound (II)

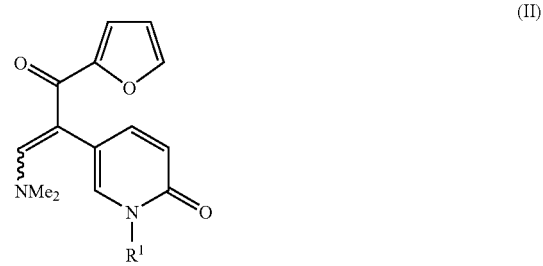

wherein $R^1$ is as defined above, to react with a compound (III)

wherein $R^2$ and $R^3$ are as defined above.
[11] A process according to [10], wherein a compound (IV)

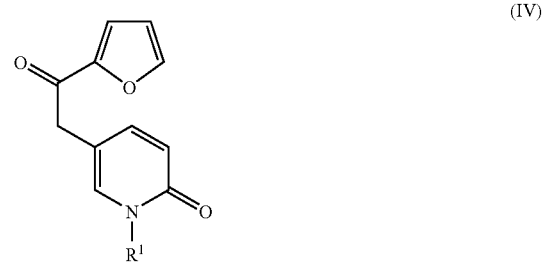

wherein R1 represent C1-6 alkyl, is allowed to react with N,N-dimethylformamide dimethyl acetal to afford the compound (II).

[12] A process according to [10], wherein a compound (V)

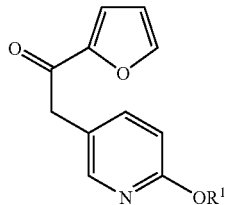
(V)

wherein R¹ represent C1-6 alkyl, is allowed to react with a compound (VI)

RX wherein R represents C1-6 alkyl and X represents halogen, to afford a compound (IV)

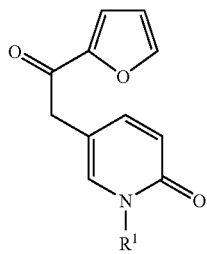
(IV)

wherein R¹ is as defined above, and the compound (IV) is allowed to react with N,N-dimethylformamide dimethyl acetal to afford the compound (II).

[13] A process according to [10], wherein a compound (VII)

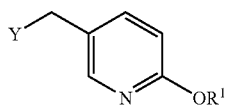
(VII)

wherein R¹ represent C1-6 alkyl and Y represent a leaving group, is allowed to react with a compound (VIII)

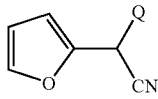
(VIII)

wherein Q represents morpholino or trimethylsilyl, to afford a compound (V)

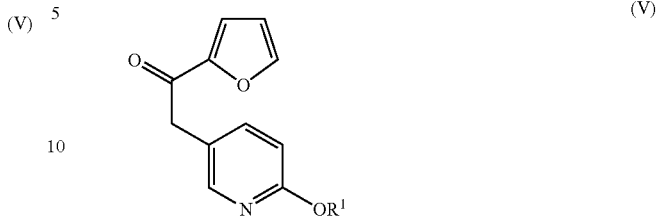
(V)

wherein R¹ is as defined above, and the compound (V) is allowed to react with a compound (VI)

RX wherein R represents C1-6 alkyl and X represents halogen, to afford a compound (IV)

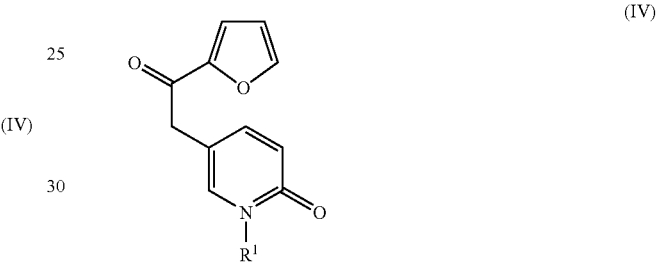
(IV)

wherein R¹ is as defined above, and the compound (IV) is allowed to react with N,N-dimethylformamide dimethyl acetal to afford the compound (II).

[14] A process according to any one of [10] to [13], wherein R¹ is methyl.
[15] A process according to any one of [10] to [14], wherein R² and R³ are hydrogen.
[16] A process according to [13], wherein Y is halogen.
[17] A process according to [13], wherein Y is chlorine.
[18] A process according to [13], wherein Q is morpholino.
[19] A process according to any one of [12] to [18], wherein the compound (VI) is added at a catalytic amount with respect to the compound (V).
[20] 5-[2-Dimethylamino-1-(furan-2-carbonyl)-vinyl]-1-methyl-1H-pyridin-2-one.
[21] 5-(2-Furan-2-yl-2-oxo-ethyl)-1-methyl-1H-pyridin-2-one.
[22] 1-Furan-2-yl-2-(6-methoxy-pyridin-3-yl)-ethanone.

The crystal form C of 5-[2-amino-4-(2-furyl)pyrimidin-5-yl]-1-methylpyridin-2(1H)-one (hereinafter referred to as simply "the crystal form C"), the crystals of 5-[2-amino-4-(2-furyl)pyrimidin-5-yl]-1-methylpyridin-2(1H)-one hydrate (hereinafter referred to as simply "the hydrate crystals") and the amorphous 5-[2-amino-4-(2-furyl)pyrimidin-5-yl]-1-methylpyridin-2(1H)-one (hereinafter referred to as simply "the amorphous compound") according to the present invention have suitable physical properties such as good solubility and are suitable for using as an active ingredient of a preventing and therapeutic agent for diseases such as constipation.

Furthermore, the processes for preparing 5-[2-amino-4-(2-furyl)pyrimidin-5-yl]-1-methylpyridin-2(1H)-one according to the present invention have advantage of fewer steps and less amount of alkyl halides used and are industrially advantageous.

DESCRIPTION OF THE PREFERRED EMBODIMENTS

Crystal Form C

Figure 1:
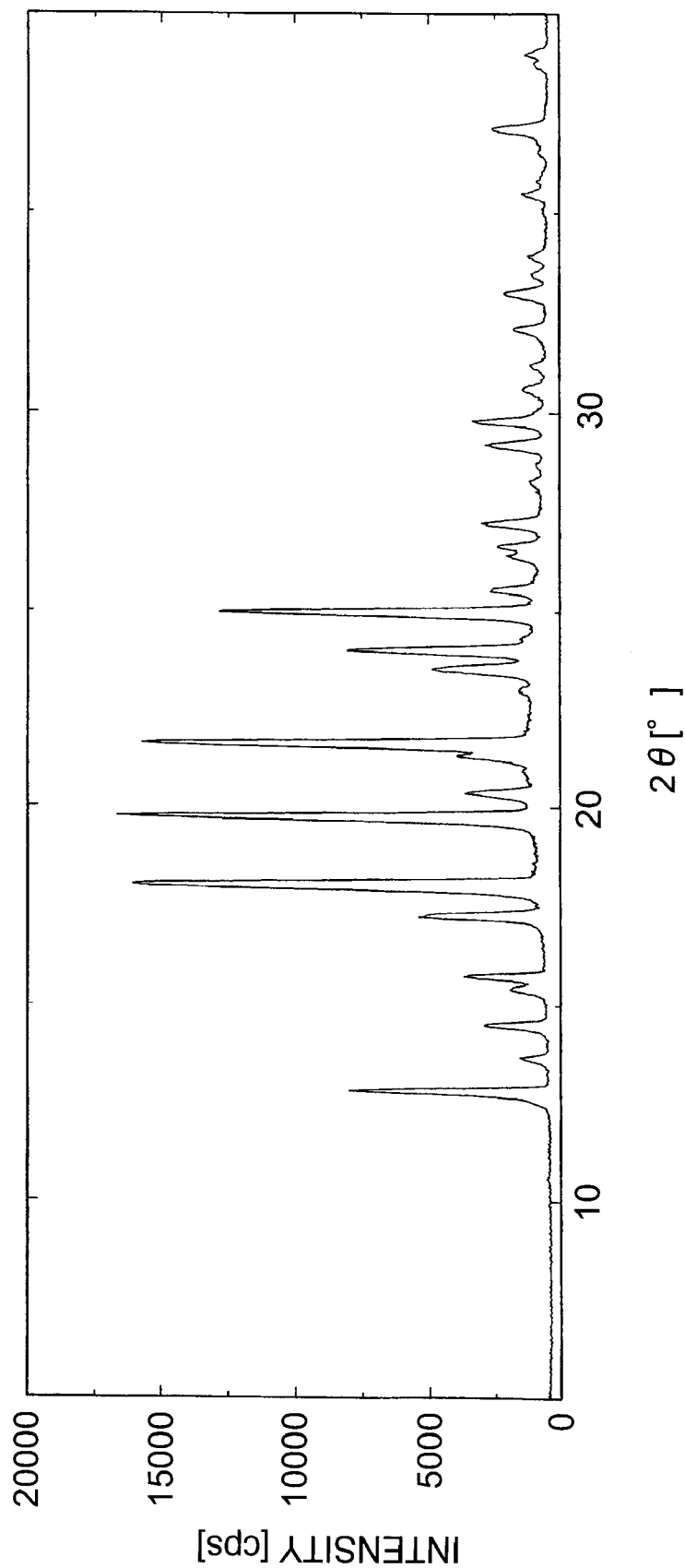
FIG. 1 is a drawing representing a powder X-ray diffraction pattern of the crystals obtained in Comparative Example 1.
Figure 2:
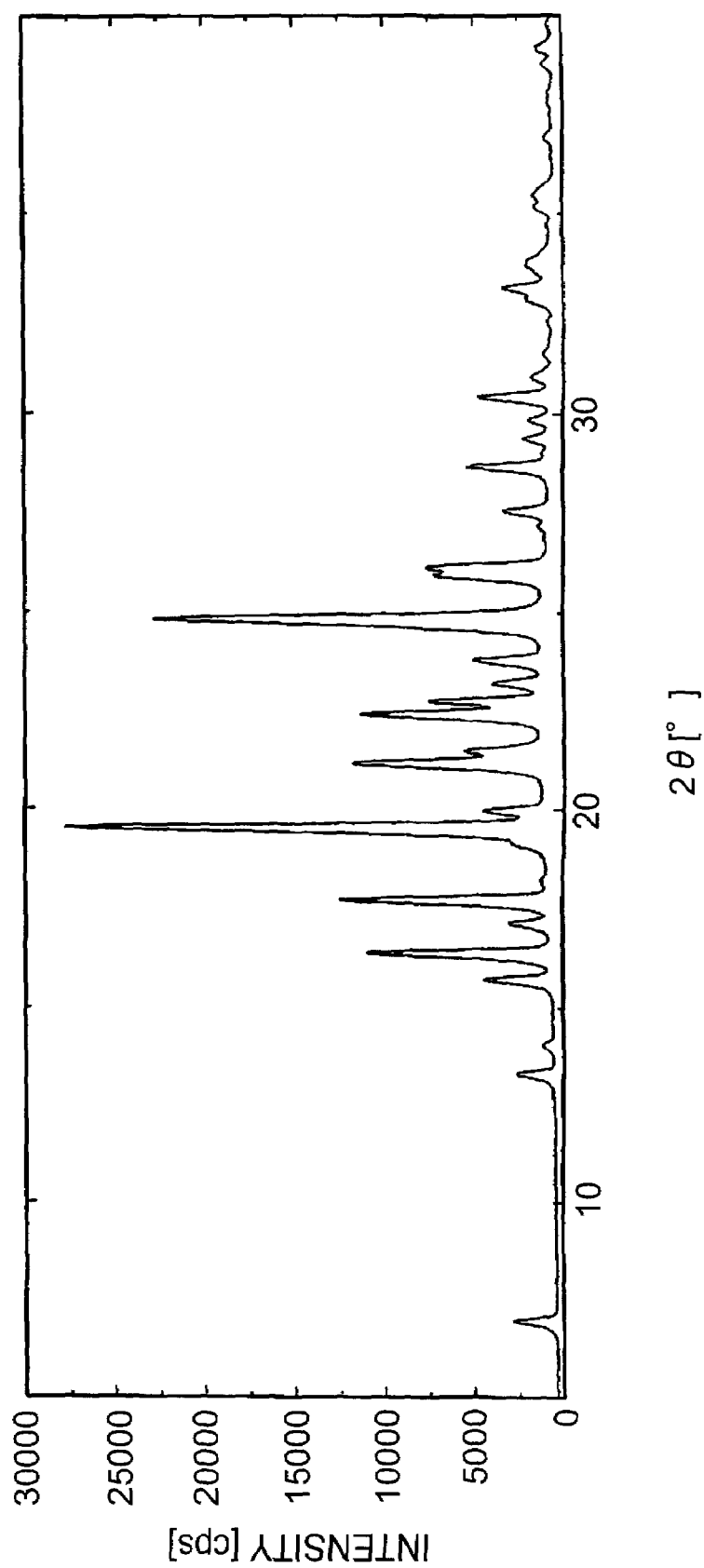
FIG. 2 is a drawing representing a powder X-ray diffraction pattern of the crystals obtained in Comparative Example 2.
Figure 3:
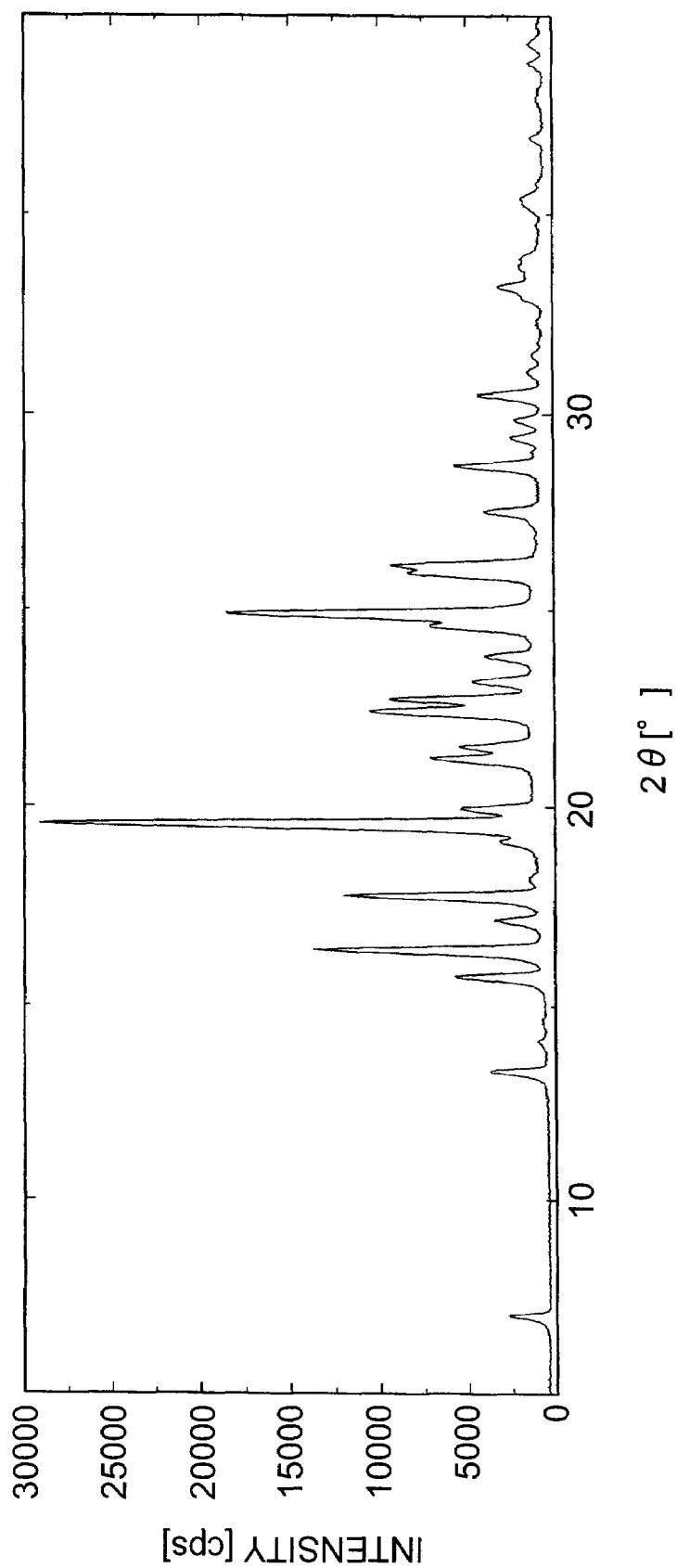
FIG. 3 is a drawing representing a powder X-ray diffraction pattern of the crystals obtained in Comparative Example 3.
Figure 4:
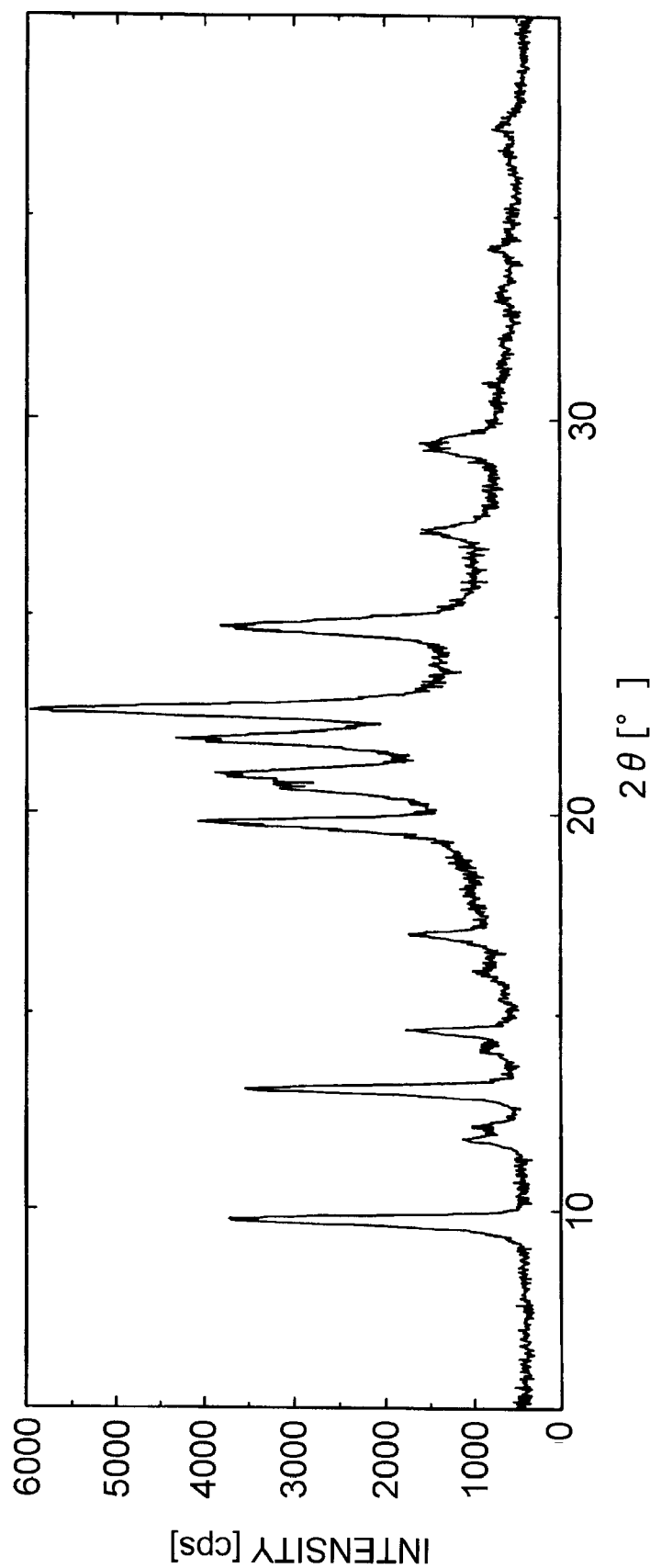
FIG. 4 is a drawing representing a powder X-ray diffraction pattern of the crystals obtained in Example 4A.
Figure 9:
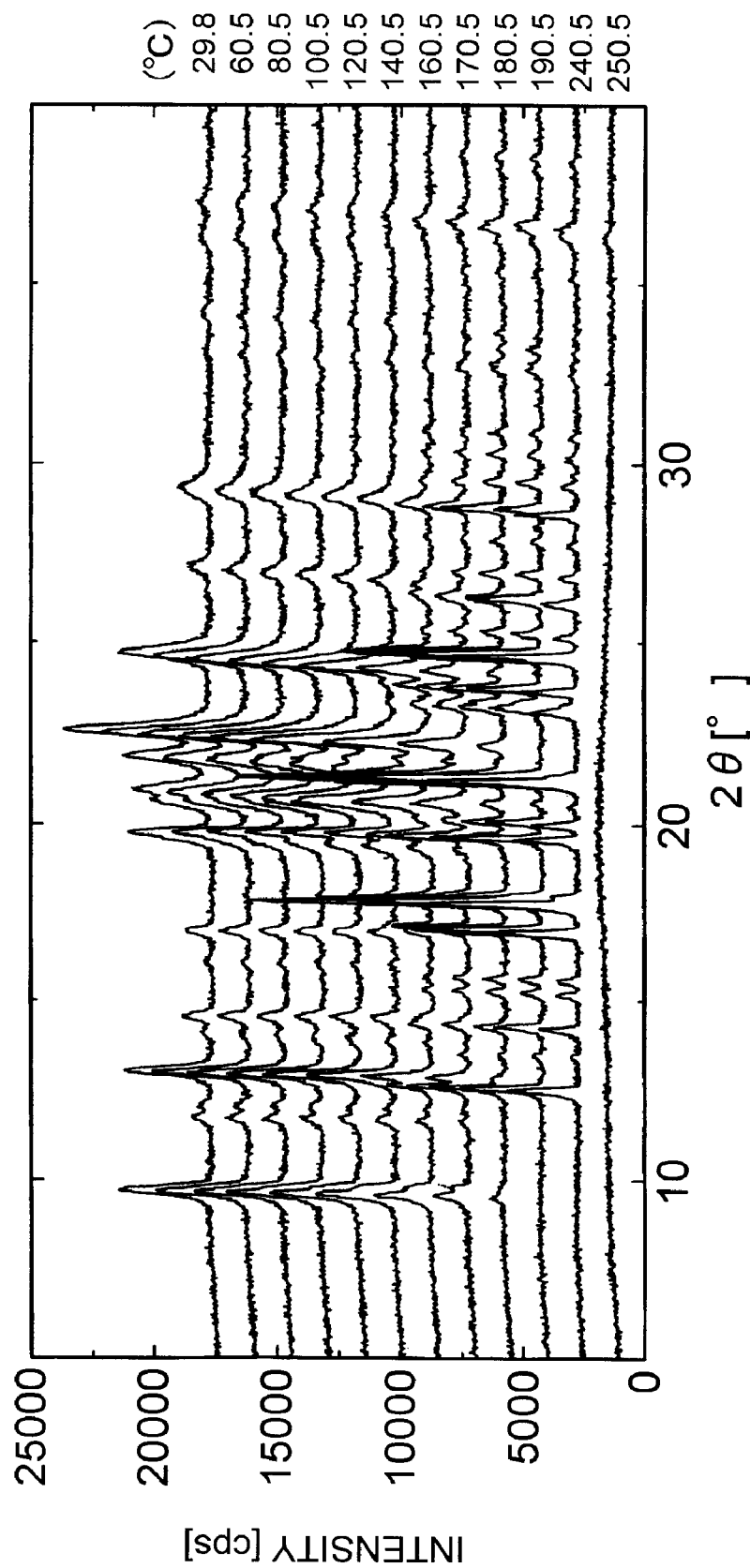
FIG. 9 is a drawing representing temperature-dependent changes of powder X-ray diffraction patterns of the crystals obtained in Example 4A.
Figure 16:
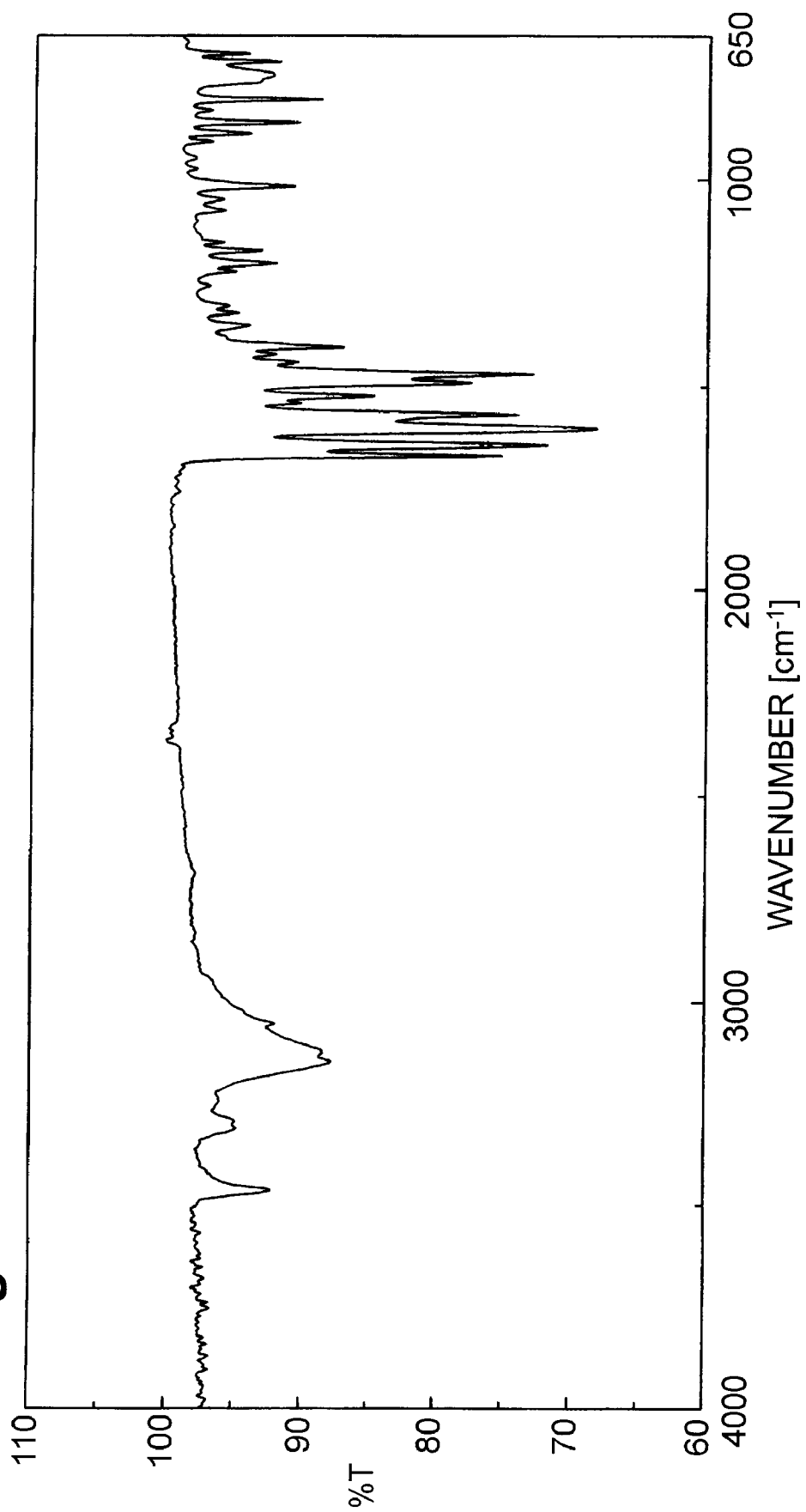
FIG. 16 is a drawing representing an infrared absorption spectrum of the crystals obtained in Example 4A.

The crystals (the crystal form C) of 5-[2-amino-4-(2-furyl)pyrimidin-5-yl]-1-methylpyridin-2(1H)-one according to the invention are characterized by having a diffraction peak at a diffraction angle (2θ±0.2°) of 9.7° and/or 21.9° in a powder X-ray diffraction and characterized by having a peak at a chemical shift of approximately 134.9 ppm and/or approximately 146.3 ppm in a $^{13}C$ solid-state NMR spectrum. These characteristic peaks in a powder X-ray diffraction and a $^{13}C$ solid-state NMR spectrum are not observed for the crystals disclosed in patent document 1, example 16 (the crystal form B). Typical powder X-ray diffraction pattern and $^{13}C$ solid-state NMR spectrum for the crystal form C are shown in FIG. 4 and FIG. 9, respectively. A typical infrared absorption spectrum for the crystal form C is shown in FIG. 16. The crystal form C is superior in solubility than the crystal form B.

Since the diffraction angle (2θ) in a powder X-ray diffraction generally has a diffraction angle error in the range of ±0.2°, the aforementioned values for the diffraction angle must be interpreted as including values within a range of ±0.2°. Thus, the present invention encompasses not only crystals whose peak diffraction angle in a powder X-ray diffraction matches exactly, but also crystals whose peak diffraction angle matches with an error of ±0.2°.

Specifically, throughout the present specification, "having a diffraction peak at a diffraction angle (2θ±0.2°) of 9.7°" means "having a diffraction peak at a diffraction angle (2θ) in the range of 9.5°-9.9°", "having a diffraction peak at a diffraction angle (2θ±0.2°) of 21.9°" means "having a diffraction peak at a diffraction angle (2θ) in the range of 21.7°-22.1°". "Having a diffraction peak at a diffraction angle (2θ±0.2°) of 9.7° and/or 21.9°" means having at least one of the above diffraction peaks.

Throughout the present specification, "having a peak at a chemical shift of approximately 134.9 ppm" means "having a peak substantially equivalent to a chemical shift of 134.9 ppm, when a $^{13}C$ solid state NMR spectrum is measured under ordinary measuring conditions", and "having a peak at a chemical shift of approximately 146.3 ppm" means "having a peak substantially equivalent to a chemical shift of 146.3 ppm, when a $^{13}C$ solid state NMR spectrum is measured under ordinary measuring conditions". "Having a peak at a chemical shift of approximately 134.9 ppm and/or approximately 146.3 ppm" means having at least one of the above peaks.

Process for Preparing the Crystal Form C

The process for preparing the crystal form C of the invention is characterized by heating and drying amorphous 5-[2-amino-4-(2-furyl)pyrimidin-5-yl]-1-methylpyridin-2(1H)-one at a high-temperature region. The amorphous 5-[2-amino-4-(2-furyl)pyrimidin-5-yl]-1-methylpyridin-2(1H)-one is obtainable by the preparing process described below.

Drying at a high-temperature region means standing at a temperature of 40 to 80° C. for 12 to 24 hours, preferably standing at 60° C. for 20 hours.

Hydrate Crystals

Figure 5:
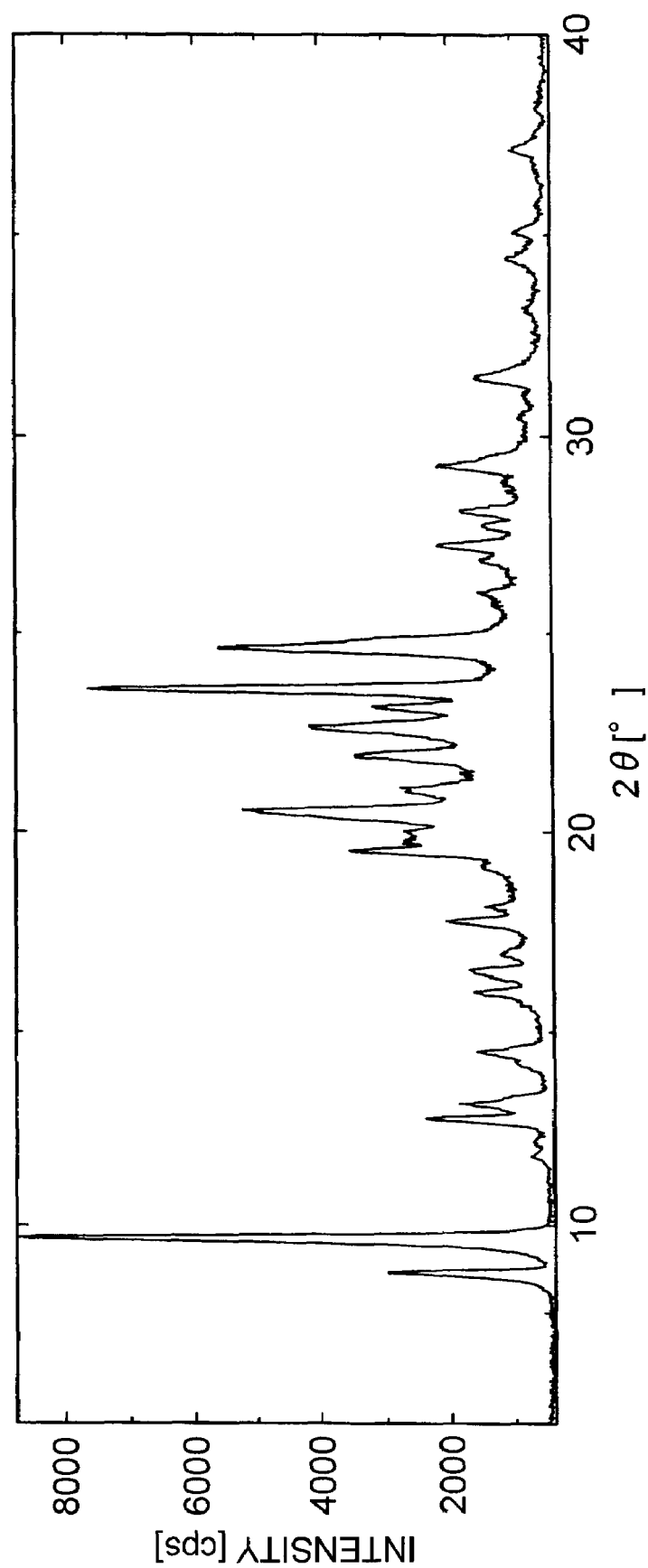
FIG. 5 is a drawing representing a powder X-ray diffraction pattern of the crystals obtained in Example 5.
Figure 6:
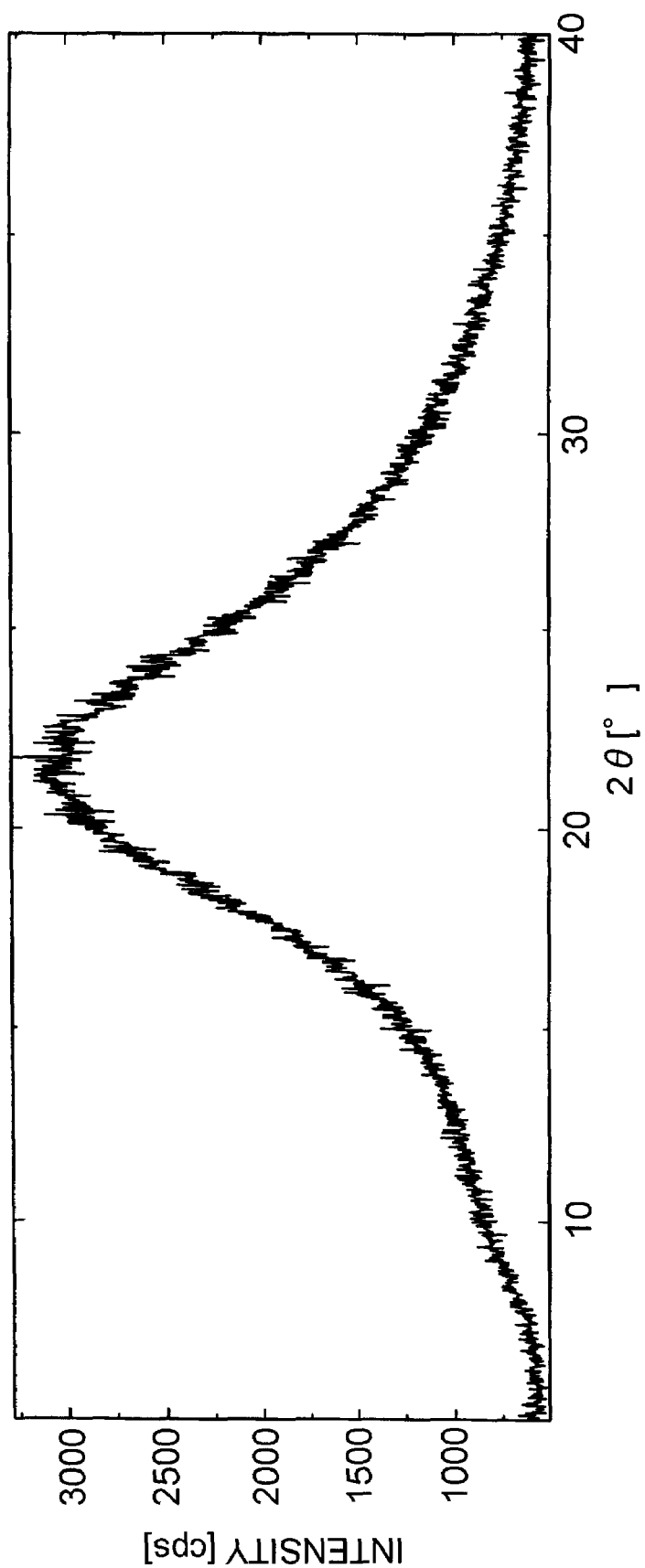
FIG. 6 is a drawing representing a powder X-ray diffraction pattern of the crystals obtained in Example 6.

The crystals of 5-[2-amino-4-(2-furyl)pyrimidin-5-yl]-1-methylpyridin-2(1H)-one hydrate according to the invention are preferably crystals of monohydrate, and are preferably characterized by having a diffraction peak at a diffraction angle (2θ±0.2°) of 8.8° in a powder X-ray diffraction. A typical powder X-ray diffraction pattern of the hydrate crystals is shown in FIG. 5. The hydrate crystals are superior in solubility than the crystal form B.

Throughout the present specification, "having a diffraction peak at a diffraction angle (2θ±0.2°) of 8.8°" means "having a diffraction peak at a diffraction angle (2θ) in the range of 8.6°-9.0°"

Process for Preparing the Hydrate Crystals

The process for preparing the hydrate crystals of the invention is characterized by humidifying a crystal form C of 5-[2-amino-4-(2-furyl)pyrimidin-5-yl]-1-methylpyridin-2(1H)-one.

Conditions for the humidification means standing in an atmosphere keeping a relative humidity of 90 to 100%, at 1 to 30° C. for 12 to 36 hours, and preferably standing in an atmosphere of a relative humidity of 95%, at 1 to 30° C. for 24 hours. Humidification is preferably carried out under a nitrogen stream.

Amorphous Compound

The amorphous 5-[2-amino-4-(2-furyl)pyrimidin-5-yl]-1-methylpyridin-2(1H)-one is superior in solubility than the crystal form B.

Process for Preparing the Amorphous Compound

The process for preparing the amorphous compound according to the invention is characterized by lyophilizing a solution of 5-[2-amino-4-(2-furyl)pyrimidin-5-yl]-1-methylpyridin-2(1H)-one. 5-[2-Amino-4-(2-furyl)pyrimidin-5-yl]-1-methylpyridin-2(1H)-one used may be in any form. That is, it may be a hydrate or anhydrate, amorphous or crystalline (including combinations of multiple crystal forms) compound, or a mixture thereof. 5-[2-Amino-4-(2-furyl)pyrimidin-5-yl]-1-methylpyridin-2(1H)-one can be prepared by the method disclosed in patent document 1, and also by the method described in Preparation Examples 1 to 6 below.

The solvent used for dissolution of 5-[2-amino-4-(2-furyl) pyrimidin-5-yl]-1-methylpyridin-2(1H)-one is not restricted so long as it dissolves the starting material to some extent, and is for example a single solvent or a mixed solvent of two or more selected from a group consisting of an alcoholic solvent such as methanol, ethanol, 2-propanol and n-propanol, an amide solvent such as acetonitrile and N,N-dimethylformamide, an ester solvent such as ethyl acetate and water. Preferred solvent is a mixed solvent of an alcoholic solvent such as methanol, ethanol and t-butyl alcohol and water, more preferable solvent is a mixed solvent of t-butyl alcohol and water, and the most preferable solvent is a mixed solvent of t-butyl alcohol and water with a mixing ratio of 1:1.

The lyophilization can be carried out under conditions usually known to those skilled in the art. For example, after the solution is frozen, the temperature is gradually or stepwise raised from around −80° C. up to around room temperature in a freeze-dryer.

Pharmaceutical Composition Comprising the Crystal Form C, the Hydrate Crystals or the Amorphous Compound The use of 5-[2-amino-4-(2-furyl)pyrimidin-5-yl]-1-methylpyridin-2(1H)-one as a therapeutic agent for constipation is disclosed in detail in patent document 1, and the crystal form C, the hydrate crystals and the amorphous compound may be used in a similar fashion as the active ingredient of a therapeutic agent for constipation. The entirety of the disclosure of patent document 1 is incorporated by reference into the disclosure of the present specification. Moreover, the crystal form C, the hydrate crystals and the amorphous compound has satisfactory stability and physical properties and are hence the most suitable form for use of 5-[2-amino-4-(2-furyl)pyrimidin-5-yl]-1-methylpyridin-2(1H)-one as the active ingredient of a therapeutic agent for constipation.

The crystal form C, the hydrate crystals or the amorphous compound may be formulated by an ordinary method into tablets, powder, fine powder, granules, coated tablets, capsules, syrup, lozenges, an inhalant, suppository, injection, ointment, eye ointment, eye drop, nose drop, ear drop, pap, lotion or the like. For formulation there may be employed commonly used excipients, binders, lubricants, coloring agents, taste correctives and, if necessary, stabilizers, emulsifiers, absorption accelerators, surfactants, pH adjustors, antiseptics, antioxidants and the like, while other components ordinarily used as starting materials for drug formulation may also be added according to common procedures.

As examples of such components there may be mentioned animal or vegetable oils such as soybean oil, beef tallow and synthetic glycerides; hydrocarbons such as liquid paraffin, squalene and solid paraffin; ester oils such as octyldodecyl myristate and isopropyl myristate; higher alcohols such as cetostearyl alcohol and behenyl alcohol; silicone resins; silicone oils; surfactants such as polyoxyethylene fatty acid ester, sorbitan fatty acid ester, glycerin fatty acid ester, polyoxyethylenesorbitan fatty acid ester, polyoxyethylene hydrogenated castor oil and polyoxyethylene-polyoxypropylene block copolymer; water-soluble polymers such as hydroxyethylcellulose, polyacrylic acid, carboxyvinyl polymer, polyethylene glycol, polyvinylpyrrolidone and methylcellulose; lower alcohols such as ethanol and isopropyl alcohol; polyhydric alcohols such as glycerin, propylene glycol, dipropylene glycol and sorbitol; sugars such as glucose and sucrose; inorganic powders such as silicic anhydride, magnesium aluminum silicate and aluminum silicate, purified water, and the like.

As examples of excipients there may be mentioned lactose, corn starch, white soft sugar, glucose, mannitol, sorbit, crystalline cellulose, silicon dioxide and the like, as examples of binders there may be mentioned polyvinyl alcohol, polyvinyl ether, methylcellulose, ethylcellulose, gum Arabic, tragacanth gum, gelatin, shellac, hydroxypropylmethylcellulose, hydroxypropylcellulose, polyvinylpyrrolidone, polypropylene glycol-polyoxyethylene block polymer, meglumine and the like, as examples of disintegrators there may be mentioned starch, agar, gelatin powder, crystalline cellulose, calcium carbonate, sodium hydrogencarbonate, calcium citrate, dextrin, pectin, carboxymethylcellulose calcium and the like, as examples of lubricants there may be mentioned magnesium stearate, talc, polyethylene glycol, silica, hydrogenated vegetable oils and the like, as examples of coloring agents there may be mentioned those approved for addition to pharmaceuticals, and as examples of taste correctives there may be mentioned cocoa powder, menthol, aromatic powder, peppermint oil, camphor, cinnamon powder and the like.

For production of an oral preparation, the crystal form C, the hydrate crystals or the amorphous compound may be combined with an excipient and, if necessary, a binder, disintegrator, lubricant, coloring agent, taste corrective or the like and then made into a powder, fine powder, granules, tablets, coated tablets or capsules.

Also, there is no restriction against sugar-coating and, if necessary, other appropriate coating of the tablets or granules.

For production of a liquid preparation such as a syrup or pharmaceutical preparation for injection, the crystal form C, hydrate crystals or amorphous compound may be combined with a pH adjustor, solubilizer, isotonizing agent or the like, and if necessary, with a dissolving aid, stabilizers or the like, and formulated by an ordinary method.

The method of producing an external preparation is not particularly restricted, and may be according to an ordinary method. Specifically, as base materials for pharmaceutical preparation there may be used various materials ordinarily employed for pharmaceuticals, quasi drugs, cosmetics and the like. As examples of specific base materials to be used there may be mentioned materials such as animal and vegetable oils, mineral oils, ester oils, waxes, higher alcohols, fatty acids, silicone oils, surfactants, phospholipids, alcohols, polyhydric alcohols, water-soluble polymers, clay minerals, purified water and the like, and if necessary there may also be added pH adjustors, antioxidants, chelating agents, antiseptic/mildew resistant agents, coloring agents, aromatics and the like, although base materials for an external preparation of the invention are not limited to these. If necessary there may also be included components such as circulation promoters, bactericidal agents, antiflash agents, cell activators, vitamins, amino acids, humectants, keratolytic agents and the like. The amounts of such base materials are the amounts which give concentrations indicated for production of ordinary external preparations.

The form of administration of the crystal form C, the hydrate crystals or the amorphous compound is not particularly restricted, and may be oral administration or parenteral administration by an ordinarily employed method. For example, the crystals may be administered after formulation into tablets, powder, granules, capsules, syrup, lozenges, an inhalant, suppository, injection, ointment, eye ointment, eye drop, nose drop, ear drop, pap, lotion or the like. The dosage of a pharmaceutical according to the invention may be appropriately selected depending on patient age, gender, body weight, severity of symptoms, particular type of condition, and on the type of dosage form or salt. For example, it will generally be administered once or divided over several times at about 30 μg to 10 g, preferably 100 μg to 5 g, more preferably 100 μg to 100 mg per day for adults in the case of oral administration or 30 μg to 1 g, preferably 100 μg to 500 mg, more preferably 100 μg to 30 mg per day in the case of injection administered once or divided over several times a day.

Process for Preparing the Compound (I)

The process for preparing the compound (I)

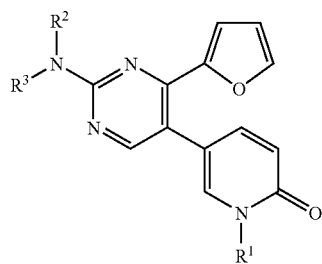

wherein $R^1$ represents C1-6 alkyl and $R^2$ and $R^3$ independently represent hydrogen or C1-6 alkyl, according to the present invention is characterized by allowing a compound (II)

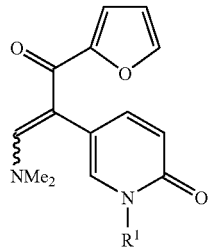

wherein $R^1$ is as defined above, to react with a compound (III)

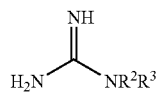

wherein $R^2$ and $R^3$ are as defined above. This preparing process has an advantage of fewer steps than the conventional preparing process (the preparing process describe in patent document 1).

As examples of the "C1-6 alkyl", there may be mentioned straight-chain or branched-chain groups such as methyl, ethyl, n-propyl, isopropyl, n-butyl, isobutyl, s-butyl, t-butyl, n-pentyl, isopentyl, s-pentyl, t-pentyl, 2-methylbutyl, 1-methylbutyl, 2-methylbutyl, neopentyl, 1,1-dimethylpropyl, 1,2-dimethylpropyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, among which C1-4 groups are preferred, methyl, ethyl or t-butyl is more preferred.

$R^1$ is preferably methyl, and $R^2$ and $R^3$ are preferably hydrogen.

The solvent used for the reaction of the compound (II) and the compound (III) is not restricted so long as it dissolves the starting materials to some extent and does not inhibit the reaction, for example, there may be mentioned N,N-dimethylformamide, 1-methyl-2-pyrrolidone, N,N'-dimetylindanone and acetonitrile. The compound (III) may be used 1.0 to 3.0 equivalents with respect to the compound (II). The reaction may be carried out in the presence of a base such as 1,8-diazabicyclo[5.4.0]undec-7-ene. The base may be used 1.5 to 3.0 equivalents with respect to the compound (II). The reaction time may be 1.5 to 48 hours. The reaction temperature may be 25 to 80° C.

The compound (II) is preferably obtained by allowing a compound (IV)

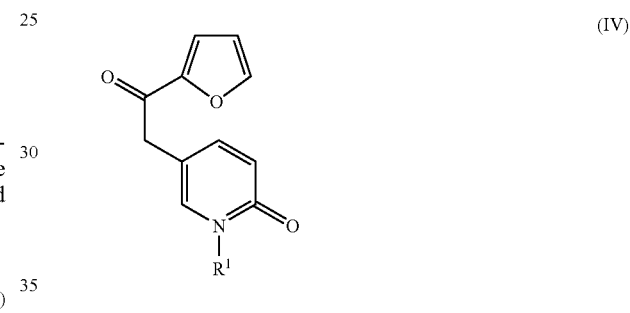

wherein R1 represent C1-6 alkyl, to react with N,N-dimethylformamide dimethyl acetal. The solvent used for the reaction of the compound (IV) and N,N-dimethylformamide dimethyl acetal is not restricted so long as it dissolves the starting materials to some extent and does not inhibit the reaction, for example, there may be mentioned N,N-dimethylformamide, 1-metyl-2-pyrrolidone, N,N'-dimetylindanone and acetonitrile. N,N-Dimethylformamide dimethyl acetal may be used 1.5 to 3.0 equivalents with respect to the compound (IV). The reaction time may be 2 to 22 hours. The reaction temperature may be 60 to 80° C. To a reaction mixture in which the compound (IV) is allowed to react with N,N-dimethylformamide dimethyl acetal to produce the compound (II) may be added the compound (III), without isolating the compound (II), to afford the compound (I).

The compound (IV) is preferably obtained by allowing a compound (V)

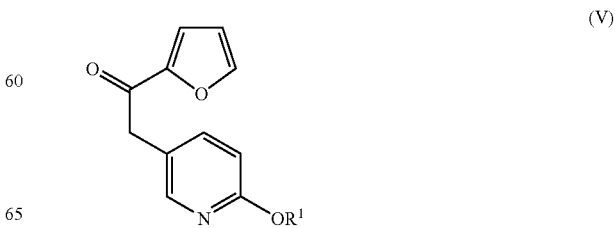

wherein R¹ represent C1-6 alkyl, to react with a compound (VI)

RX wherein R represents C1-6 alkyl and X represents halogen.

Halogen is fluorine, chlorine, bromine or iodine. R is preferably methyl, and X is preferably iodine.

The solvent used for the reaction of the compound (V) and the compound (VI) is not restricted so long as it dissolves the starting materials to some extent and does not inhibit the reaction, for example, there may be mentioned N,N-dimethylformamide, 1-metyl-2-pyrrolidone, N,N'-dimetylindanone, dimethylsulfoxide and t-butyl alcohol. The compound (VI) is preferably used at a catalytic amount with respect to the compound (V), and more preferably used 0.3 to 1.0 equivalents. The reaction time may be 3 to 7 hours. The reaction temperature may be 80 to 100° C.

The compound (V) is preferably obtained by allowing a compound (VII)

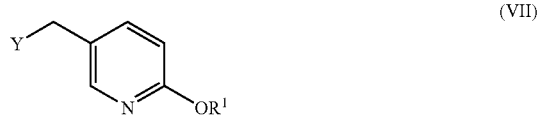

wherein R¹ represent C1-6 alkyl and Y represent a leaving group, to react with a compound (VIII)

wherein Q represents morpholino or trimethylsilyl.

Y means a leaving group such as halogen, mesyloxy or trifluoromethyloxy, and is preferably halogen and more preferably chlorine. Q is preferably morpholino.

The solvent used for the reaction of the compound (VII) and the compound (VIII) is not restricted so long as it dissolves the starting materials to some extent and does not inhibit the reaction, for example, there may be mentioned tetrahydrofuran, 1,2-dimethoxyethane, t-butyl methyl ether and toluene. The compound (VIII) may be used 1.05 to 1.15 equivalents with respect to the compound (VII). The reaction time may be 1 to 3 hours. The reaction temperature may be −20 to 0° C.

Where the compound (I) is 5-[2-amino-4-(2-furyl)pyrimidin-5-yl]-1-methylpyridin-2(1H)-one, the following compounds are useful as intermediates: 5-[2-dimethylamino-1-(furan-2-carbonyl)-vinyl]-1-methyl-1H-pyridin-2-one, 5-(2-furan-2-yl-2-oxo-ethyl)-1-methyl-1H-pyridin-2-one and 1-furan-2-yl-2-(6-methoxy-pyridin-3-yl)-ethanone.

EXAMPLES

Preparation Example 1

Synthesis of (6-methoxypyridin-3-yl)methanol (2)

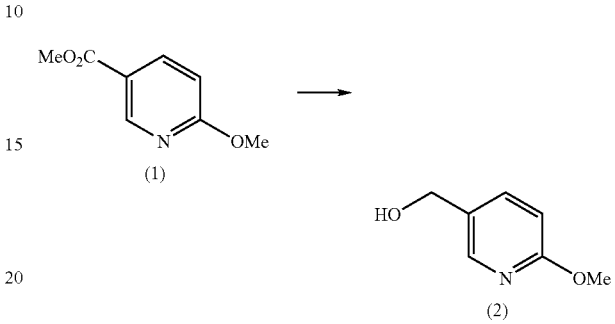

To a solution of methyl-6-methoxynicotinate (1) (650 g, 3.89 mol) in t-butyl methyl ether (hereinafter abbreviated as "MTBE") (6.5 L) cooled in an ice bath was added sodium bis(2-methoxyethoxy)aluminum hydride (65% solution in toluene, 1.45 kg, 4.67 mol) under a nitrogen atmosphere over a period of 1.3 hours. After stirring for 20 minutes, a 3.5 N aqueous solution of sodium hydroxide (2.6 L) was added to the reaction mixture while keeping the temperature 15° C. or below. The reaction mixture was stirred at 32° C. for 45 minutes and then the organic layer was separated and the aqueous layer was re-extracted with MTBE (2.3 L). The organic layers were combined and concentrated under reduced pressure to dryness, and then toluene (1.3 L) was added to the residue and azeotropic distillation was carried out. Azeotropic distillation with toluene (1.3 L) was repeated three times to give 597 g of the title compound as a pale yellow oil (yield 100%).

¹H-NMR (CDCl₃) δ (ppm): 8.11 (1H, d, J=2.4 Hz), 7.62 (1H, dd, J=2.4 Hz, 8.8 Hz), 6.75 (1H, d, J=8.8 Hz), 4.62 (2H, s), 3.93 (3H, s)

Preparation Example 2

Synthesis of 5-chloromethyl-2-methoxypyridine (3)

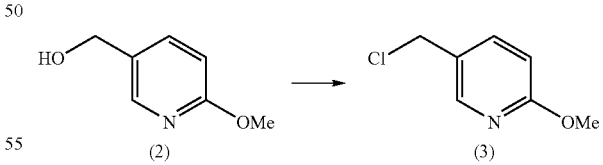

To a solution of (6-methoxypyridin-3-yl)methanol (2) (537.8 g, 3.86 mol) obtained in Preparation Example 1 in dimethylformamide (1.6 L) was added dropwise thionyl chloride (310 mL, 4.25 mol) over a period of 1.3 hours while cooling in an ice bath under a nitrogen atmosphere. After stirring for 1 hour while cooling in an ice bath, toluene (5.4 L) and a 2N aqueous solution of sodium hydroxide (5.4 L) were added successively to the reaction mixture at 23° C. or below. The reaction mixture was stirred for about 10 minutes and then the aqueous layer was separated, the organic layer was washed with water (2.7 L). The organic layer was concentrated under reduced pressure to dryness, and then toluene (1.0 L) was added to the residue and azeotropic distillation was carried out to give 618.8 g of the title compound as a pale yellow oil (content 556.3 g, yield 91.4%).

$^1$H-NMR (CDCl$_3$) δ (ppm): 8.15 (1H, d, J=2.4 Hz), 7.63 (1H, dd, J=2.4 Hz, 8.4 Hz), 6.75 (1H, d, J=8.4 Hz), 4.55 (2H, s), 3.94 (3H, s)

Preparation Example 3

Synthesis of furan-2-yl-morpholin-4-yl-acetonitrile (5)

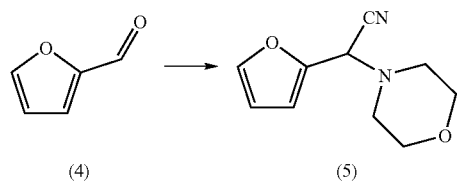

A solution of furfural (4) (550 g, 5.72 mol) in toluene (5.5 L) was cooled to 8° C, and then an aqueous solution (1.1 L water) of potassium cyanide (384.6 g, 5.72 mol) was added over a period of 7 minutes.

Then, to the reaction mixture was added an aqueous solution (1.65 L water) of p-toluenesulfonic acid monohydrate (1143.0 g, 6.01 mol) over a period of 20 minutes, and the reaction mixture was further stirred for 1 hour. To the reaction mixture was added a solution of morpholine (997 g, 11.45 mol) in toluene (100 mL) over a period of 8 minutes, followed by stirring for 2.5 hours in a water bath at 20° C. The aqueous layer was separated, and the organic layer was washed with water (2.75 L) and then concentrated under reduced pressure to dryness to give 1028.7 g of the title compound as a reddish-brown oil (content 90.2%, yield 84.3%).

$^1$H-NMR (CDCl$_3$) δ (ppm): 7.47 (1H, brs), 6.57 (1H, d, J=3.2 Hz), 6.41 (1H, dd, J=3.2 Hz, 1.6 Hz), 4.85 (1H, s), 4.43 (4H, m), 4.31 (4H, m)

Example 1

Synthesis of 1-furan-2-yl-2-(6-methoxy-pyridin-3-yl)-ethanone (7)

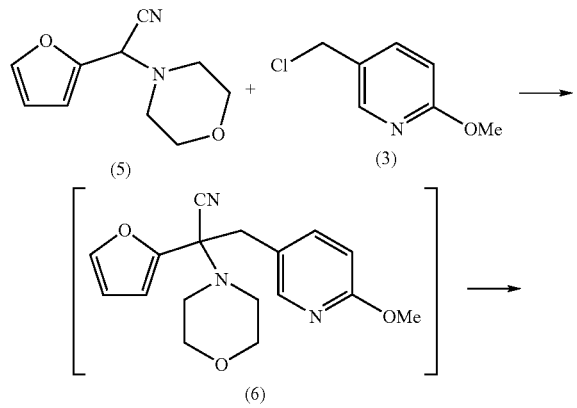

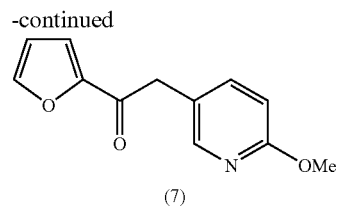

A solution of furan-2-yl-morpholin-4-yl-acetonitrile (5) (818.0 g, content 737.9 g, 3.84 mol) obtained in Preparation Example 3 and 5-chloromethyl-2-methoxypyridine (3) (611.8 g, content 550.0 g, 3.49 mol) obtained in Preparation Example 2 in toluene (4.4 L) was cooled to −15° C, and then a solution of potassium-t-butoxide (508.9 g, 4.54 mol) in tetrahydrofuran (4.4 L) was added at −5° C. or below over a period of 72 minutes, and the reaction mixture was further stirred for 1.5 hours.

Next, to the reaction mixture was added a 6N aqueous solution of hydrochloric acid (4.4 L), followed by heating to 70° C. and stirring for 2 hours. The reaction mixture was cooled to 5° C. and a 3N aqueous solution of sodium hydroxide (3.0 L) was added at 20° C. or below. The organic layer was separated, the aqueous layer was re-extracted with toluene (6.0 L), and the organic layers were combined and concentrated under reduced pressure to dryness to give 828.5 g of the title compound as a brown oil (content 647.8 g, yield 85.5%).

2-Furan-2-yl-3-(6-methoxy-pyridin-3-yl)-2-morpholin-4-yl-propionate (6)

$^1$H-NMR (CDCl$_3$) δ (ppm): 7.71 (1H, d, J=2.4 Hz), 7.48 (1H, d, J=1.6 Hz), 7.11 (1H, dd, J=2.4 Hz, 8.4 Hz), 6.56 (1H, d, J=8.4 Hz), 6.27 (2H, m), 3.87 (3H, s), 3.80 (4H, m), 3.38 (1H, d, J=13.2), 3.26 (1H, d, J=13.2), 2.78-2.81 (2H, m), 2.45-2.78 (2H, m)

1-Furan-2-yl-2-(6-methoxy-pyridin-3-yl)-ethanone (7)

$^1$H-NMR (CDCl$_3$) δ (ppm): 8.08 (1H, d, J=2.4 Hz), 7.61 (1H, d, J=1.7 Hz), 7.53 (1H, dd, J=2.4 Hz, 8.2 Hz), 7.24 (1H, d, J=3.6 Hz), 6.71 (1H, d, J=8.2 Hz), 6.55 (1H, dd, J=1.7 Hz, 3.6 Hz), 4.05 (2H, s), 3.91 (3H, s)

Example 2

Synthesis of 5-(2-furan-2-yl-2-oxo-ethyl)-1-methyl-1H-pyridin-2-one (8)

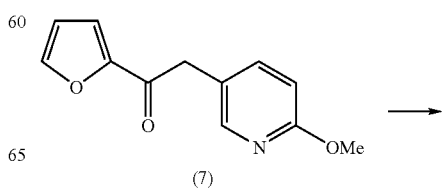

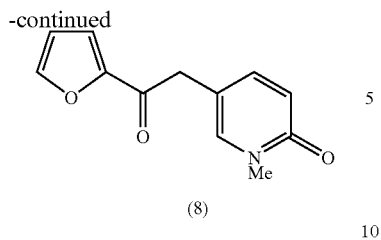

(8)

To a solution of 1-furan-2-yl-2-(6-methoxy-pyridin-3-yl)-ethanone (7) (800.0 g, content 625.6 g, 2.88 mol) obtained in Example 1 in N-methyl-2-pyrrolidine (NMP) (1.88 L) was added iodomethane (122.6 g, 0.86 mol), and the reaction mixture was stirred at 100° C. for 3 hours and then at room temperature for 17.5 hours. To the reaction mixture was added dropwise MTBE (6.6 L) over a period of 77 minutes, followed by stirring for 1 hour while cooling in an ice bath. The precipitated crystals were collected by filtration and washed with MTBE (2.0 L), and then dried under reduced pressure at 50° C. for 3 hours to give 692.0 g of a crude product of the title compound as a dark brown powder (content 536.4 g, yield 85.7%).

To the obtained crude product (682.0 g, content 528.7 g, 2.43 mol) were added 1,2-dimethoxyethane (hereinafter abbreviated as "DME") (7.93 L) and water (0.68 L), followed by heating and stirring at 80° C. for 75 minutes. After confirming dissolution, stirring was continued overnight at 8° C. The precipitated crystals were collected by filtration and washed with DME (2.0 L), and then air-dried at 60° C. for 2.3 hours to give 468.46 g of the title compound as pale yellow crystals (content 462.8 g, yield 87.5%).

$^1$H-NMR (DMSO) δ (ppm): 8.02 (1H, d, J=1.6 Hz), 7.57 (2H, m), 7.30 (1H, dd, J=3.4 Hz, 9.2 Hz), 6.74 (1H, dd, J=1.6 Hz, 3.6 Hz), 6.33 (1H, d, J=9.2 Hz), 3.98 (2H, s), 3.38 (3H, s)

Example 3A

Synthesis of 5-[2-amino-4-(2-furyl)pyrimidin-5-yl]-1-methylpyridin-2(1H)-one (10)

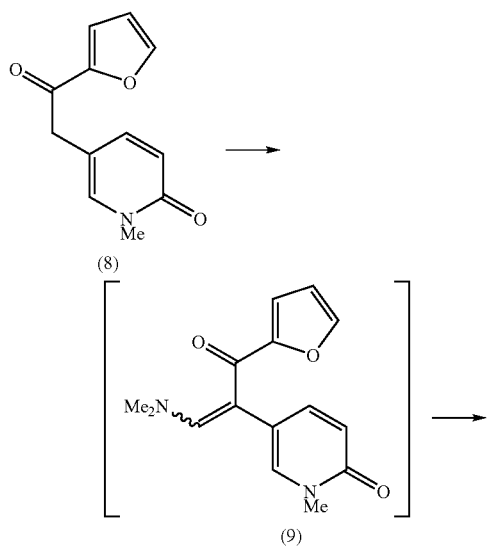

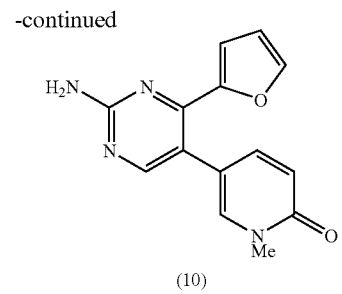

(10)

To 5-(2-furan-2-yl-2-oxo-ethyl)-1-methyl-1H-pyridin-2-one (8) (402.0 g, content 397.6 g, 1.83 mol) obtained in Example 2 were added dimethylformamide (0.4 L) and N,N-dimethylformamide dimethyl acetal (654.4 g, 5.49 mol), and the reaction mixture was stirred at 60° C. for 10.5 hours and then at room temperature for 13.5 hours. To the reaction mixture were added guanidine hydrochloride (524.56 g, 5.49 mol) and 1,8-diazabicyclo[5.4.0]undec-7-en (DBU) (821 mL, 5.49 mol), and the reaction mixture was stirred for 7.8 hours at 70° C. Next, to the reaction mixture was added 2-propanol (12.0 L), followed by stirring for 2 hours in an ice bath. The precipitated crystals were collected by filtration, washed with 2-propanol (1.0 L), and then air-dried at 60° C. for 13 hours to give 424.9 g of the title compound as pale yellow crystals (content 413.0 g, yield 84.1%).

5-[2-Dimethylamino-1-(furan-2-carbonyl)-vinyl]-1-methyl-1H-pyridin-2-one (9)

$^1$H-NMR (CDCl$_3$) δ (ppm): 7.77 (1H, s), 7.45 (1H, d, J=2.0 Hz), 7.26 (1H, dd, J=2.4 Hz, 9.2 Hz), 7.14 (1H, dd, J=2.4 Hz), 6.60 (1H, d, J=9.2 Hz), 6.50 (1H, J=3.2 Hz), 6.37 (1H, J=3.2 Hz), 3.55 (3H, s), 2.93 (6H, brs)

5-[2-Amino-4-(2-furyl)pyrimidin-5-yl]-1-methylpyridin-2(1H)-one (10)

$^1$H-NMR (DMSO) δ (ppm): 8.13 (1H, s), 7.75 (1H, dd, J=0.7 Hz, 1.4 Hz), 7.72 (1H, d, J=2.4 Hz), 7.20 (1H, dd, J=2.4 Hz, 9.0 Hz), 6.78 (2H, brs), 6.72 (1H, d, J=3.5 Hz), 6.56 (1H, m), 6.36 (1H, d, J=9.0 Hz), 3.44 (3H, s)

Preparation Example 3B

Synthesis of 5-[2-amino-4-(2-furyl)pyrimidin-5-yl]-1-methylpyridin-2(1H)-one (10)

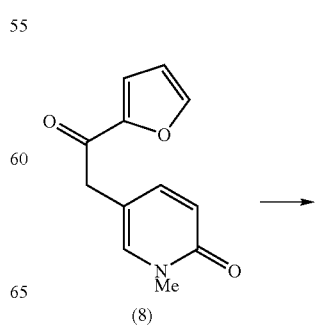

(8)

-continued

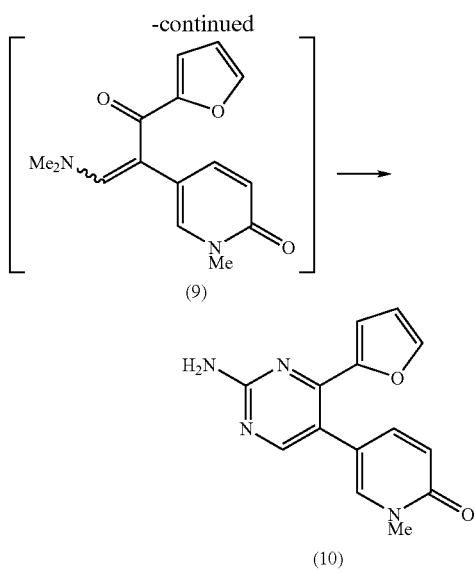

To 5-(2-furan-2-yl-2-oxo-ethyl)-1-methyl-1H-pyridin-2-one (8) (10.0 g, 46.04 mmol) obtained in Example 2 were added dimethylformamide (20 mL), N,N-dimethylformamide dimethyl acetal (9.21 mL, 69.06 mmol) and DBU (10.3 mL, 69.06 mmol), and the reaction mixture was stirred at 80° C. for about 5 hours and then allowed to cool. Next, to the reaction mixture was added 2-propanol (100 mL), and the reaction mixture was stirred at 8° C. for about 16 hours. The precipitated crystals were collected by filtration, washed with 2-propanol (45 mL), and then air-dried at 50° C. for 20 minutes to give 10.2 g of a crude product of the title compound (10) as pale yellow crystals (content 10.2 g, yield 82.3%).

Comparative Example 1

Preparation of Crystal Form A(1)

To 30 g of crude 5-[2-amino-4-(2-furyl)pyrimidin-5-yl]-1-methylpyridin-2(1H)-one (10) obtained in Example 3A were added 30 mL of 2-propanol and 150 mL of water, followed by heating and stirring for 25 minutes in an oil bath at 90° C. Upon confirming the absence of solid, filtration with heating was performed and the filtrate was heated and stirred at 70° C. for about 30 minutes. It was then heated and stirred for 1.3 hours at an external temperature of 55° C, and subsequently stirred for 2.3 hours at an external temperature of 45 to 40° C. Precipitation of crystals was confirmed at an internal temperature of approximately 47° C. The reaction mixture was further stirred at 30° C. for about 40 minutes, at room temperature for 1 hour and at 4° C. for 1.6 hours, and then the crystals were collected by filtration. The crystals were washed 3 times with 20 mL of 2-propanol and dried at 60° C. for 10.5 hours to give 19.9 g of the crystal form A.

Comparative Example 2

Preparation of the Crystal Form B(1)

To a suspension of 5-[2-amino-4-(2-furyl)pyrimidinyl]-1,2-dihydro-2-pyridinone (2.2 g, 8.65 mmol) in methanol (44 mL) was added sodium methoxide (940 mg, 17.4 mmol) at room temperature under a nitrogen atmosphere, followed by stirring. After 15 minutes, iodomethane was added (1.6 mL, 25.7 mmol), followed by stirring for 22 hours. The reaction mixture was concentrated, and water was added to the residue, and the precipitates were collected by filtration and washed with water to give crude crystals of the title compound (1.98 g). This was suspended in ethanol, and the precipitates were collected by filtration and washed with ethanol to give 5-[2-amino-4-(2-furyl)pyrimidin-5-yl]-1-methylpyridin-2(1H)-one (1.54 g, 66%) as a pale yellow solid (the crystal form B).

Comparative Example 3

Preparation of the Crystal Form B(2)

To 10 g of crude 5-[2-amino-4-(2-furyl)pyrimidin-5-yl]-1-methylpyridin-2(1H)-one (10) were added 10 mL of 2-propanol and 50 mL of water, followed by heating and stirring for about 30 minutes at an external temperature of 85° C. Upon confirming dissolution, the solution was cooled in an ice bath and stirred for 1.5 hours, and the crystals were collected by filtration. The crystals were washed twice with 10 mL of 2-propanol and dried at 60° C. for 10.5 hours to give 6.84 g of the crystal form B.

Example 4A

Preparation of the Crystal Form C(1)

After thoroughly dissolving 5.43 g of crude 5-[2-amino-4-(2-furyl)pyrimidin-5-yl]-1-methylpyridin-2(1H)-one (10) in 1 L of t-butyl alcohol/water (1:1, v/v), the mixture was filtered using a suction filter and a filter paper, and the filtrate was transferred to a stainless steel container and frozen in a freeze-dryer (Edwards Co., Ltd.; S08 middle size freeze-dryer). Pressure reduction was initiated after cooling to a shelf temperature of −40° C. After elapse of 20 hours at a pressure of 0.01 mbar, the shelf temperature was raised over a period of 25 hours until the shelf temperature reached 8° C. The pressure was then increased to atmospheric pressure, and the obtained solid was taken from the freeze-dryer and allowed to stand at 60° C. for 19 hours. It was subsequently allowed to stand at room temperature for 43 hours under a nitrogen stream to give a white solid.

Example 4B

Preparation of the Crystal Form C(2)

The crystals obtained in Comparative Example 1 (the crystal form A) (5.43 g) were dissolved in 1 L of t-butyl alcohol/water (1:1, v/v) and filtered. Then, the obtained filtrate was placed in a freeze-dryer and lyophilized. The conditions of time and temperature of lyophilization is as follows.

TABLE 1

| lyophilization time (hour) | setting temperature (° C.) |
|---|---|
| 46 | −80 |
| 16 | 10 |
| 9 | 20 |

Taken from the freeze-dryer, the amorphous compound is obtained. Then, the obtained amorphous compound (whole amount) was allowed to stand in an oven at a temperature of 60° C. for 20 hours to give crystal form C.

Example 5

Preparation of the Hydrate Crystals

By constantly flowing a nitrogen gas with a relative humidity of 95% into a desiccator, the relative humidity in the desiccator was kept approximately 95%. The crystal form C obtained in Example 4B (330 mg) was placed therein and allowed to stand at room temperature for about 24 hours to give the hydrate crystals.

Example 6

Preparation of the Amorphous Compound

The crystal form A obtained in Comparative Example 1 (1.21 g) was dissolved in 200 mL of t-butyl alcohol/water (1:1, v/v) and filtered. Then, the obtained filtrate was placed in a freeze-dryer and lyophilized. The conditions of time and temperature of lyophilization is as follows.

TABLE 2

| lyophilization time (hour) | setting temperature (° C.) |
|---|---|
| 15 | −80 |
| 24 | −20 |
| 3 | 0 |
| 24 | 10 |

Taken from the freeze-dryer, the amorphous compound is obtained.

Measurement of Powder X-ray Diffraction Pattern

The X-ray diffraction patterns of the respective crystals obtained in Comparative Example 1A, Comparative Example 2, Comparative Example 3, Example 4A, Example 5 and Example 6 (the crystal form A, the crystal form B(1), the crystal form B(2), the crystal form C, the hydrate crystals and the amorphous compound) were measured under the following conditions. The powder X-ray diffraction patterns of the respective crystals are shown in FIG. 1 to 6. Table 3 shows the characteristic diffraction (2θ) peaks for the respective crystals.
Target/tube current/tube voltage: Cu/40 kV/200 mA
Monochrometer: Curved crystal monochrometer
Counter: Scintillation counter
Scan speed: 2°/min
Scan step: 0.02°
Scanning axis: 2θ/θ
Scanning range: 5-40°
Divergence slit: 0.5°
Scattering slit: 0.5°
Receiving slit: 0.3 mm

TABLE 3

| Crystal | 2θ (°) |
|---|---|
| Crystal form A | 12.8 |
|  | 18.1 |
|  | 23.5 |
| Crystal form B | 7.0 |
|  | 16.4 |
| Crystal form C | 9.7 |
|  | 21.9 |
| Hydrate crystals | 8.8 |

Measurement of Variable-Temperature Powder X-ray Diffraction Pattern

Figure 7:
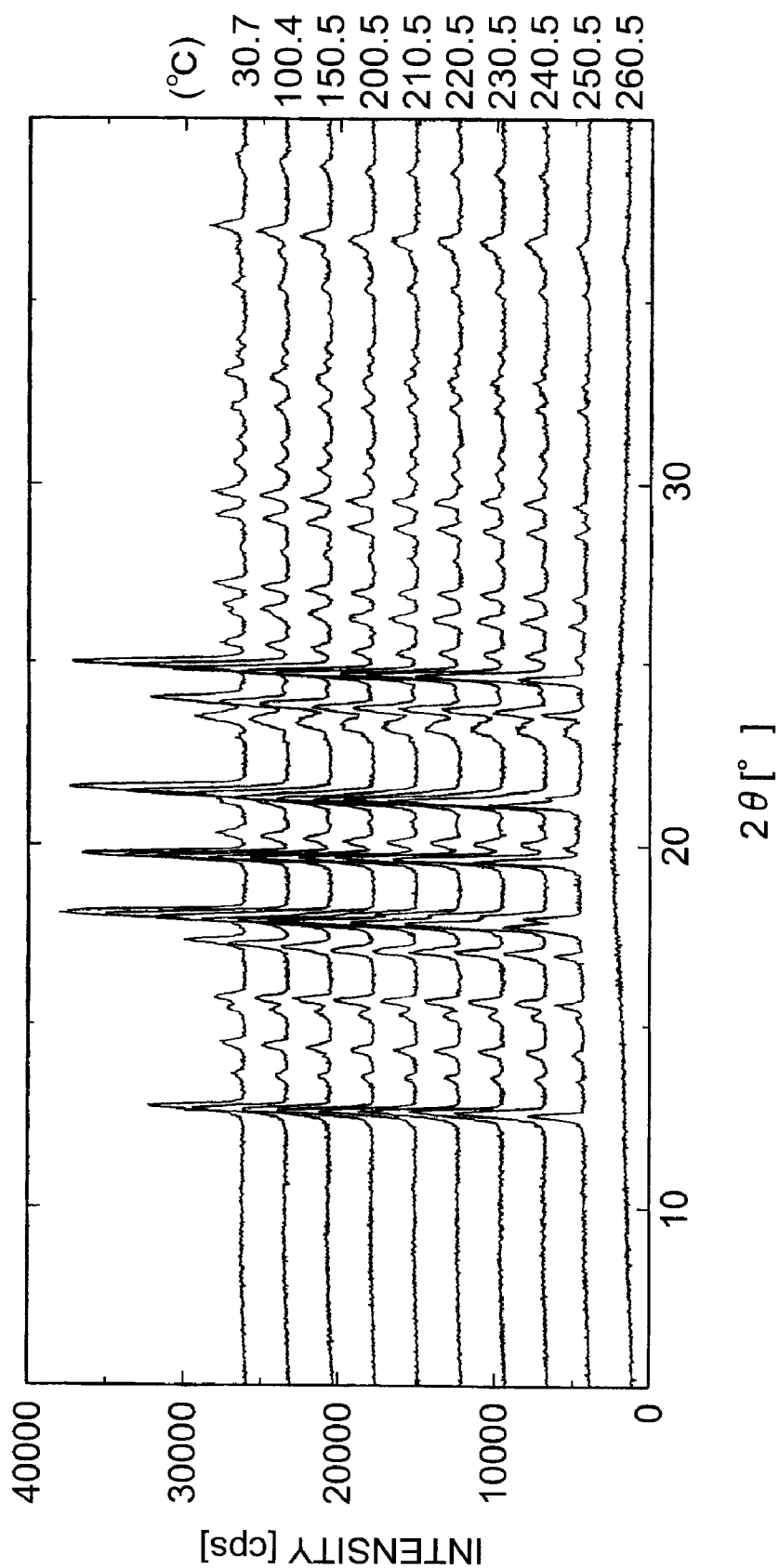
FIG. 7 is a drawing representing temperature-dependent changes of powder X-ray diffraction patterns of the crystals obtained in Comparative Example 1.
Figure 8:
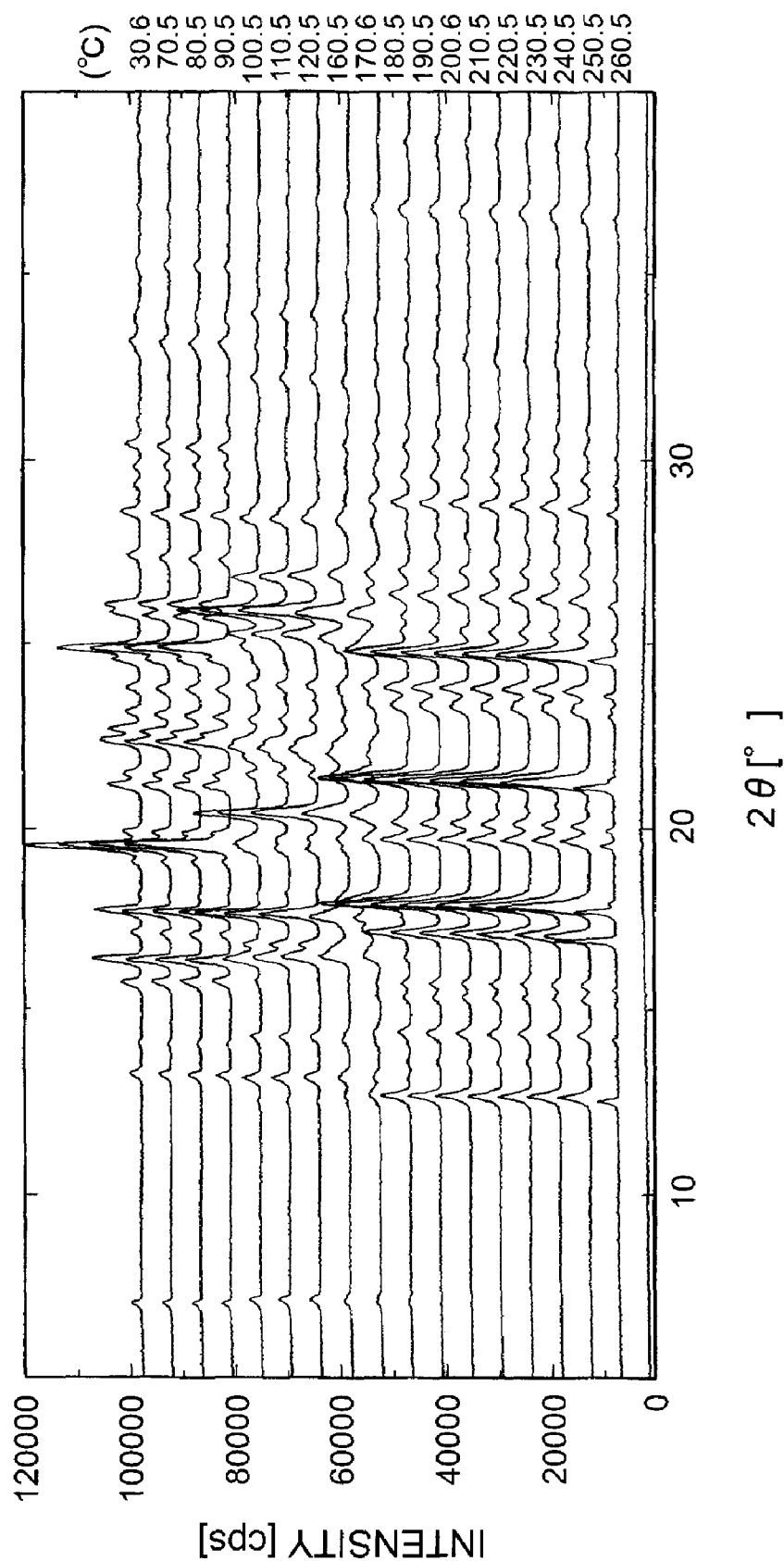
FIG. 8 is a drawing representing temperature-dependent changes of powder X-ray diffraction patterns of the crystals obtained in Comparative Example 3.

Changes in the powder X-ray diffraction pattern, with increase in the sample temperature from 30° C. to 260° C., were observed for the respective crystals obtained in Comparative Example 1, Comparative Example 3 and Example 4A (the crystal form A, the crystal form B(2) and the crystal form C). The measuring conditions were the same as for the powder X-ray diffraction pattern measurement described above, except for the measuring temperature. The temperature-dependent changes in the powder X-ray diffraction pattern of the respective crystals are shown in FIG. 7 to 9.

Thermal Analysis (Differential Scanning Calorimetry; DSC)

Figure 10:
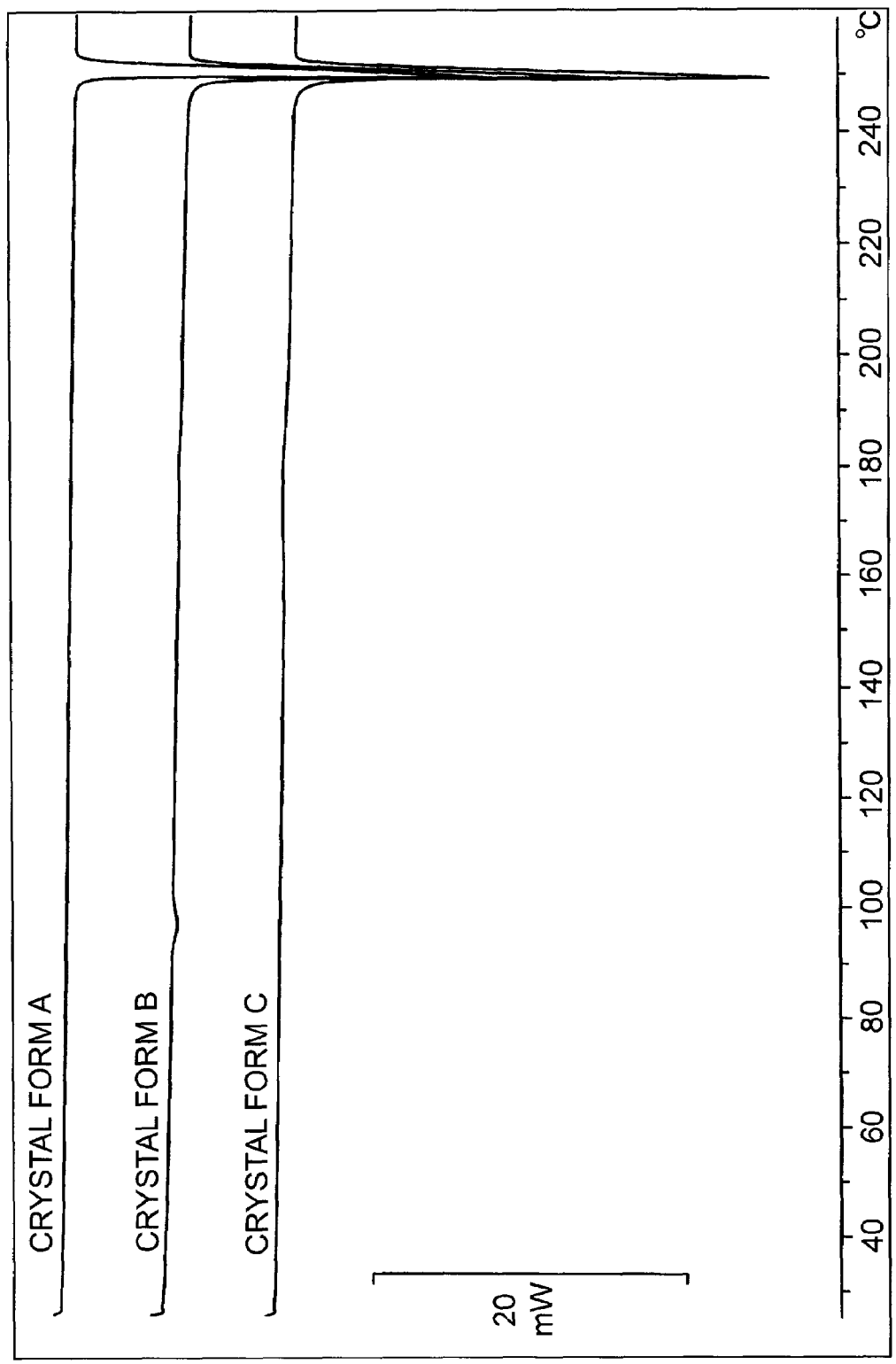
FIG. 10 is a drawing representing DSC patterns of the crystals obtained in Comparative Example 1, Comparative Example 3 and Example 4A.
Figure 11:
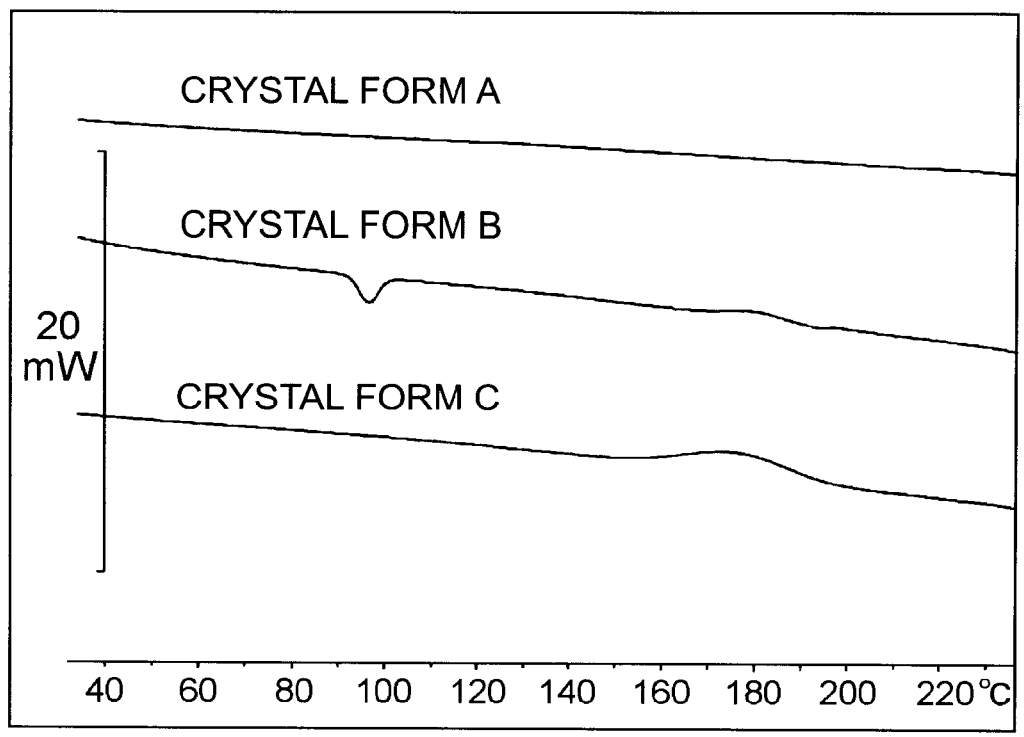
FIG. 11 is a magnification of the DSC patterns in FIG. 10 in a range of 40-230° C.
Figure 12:
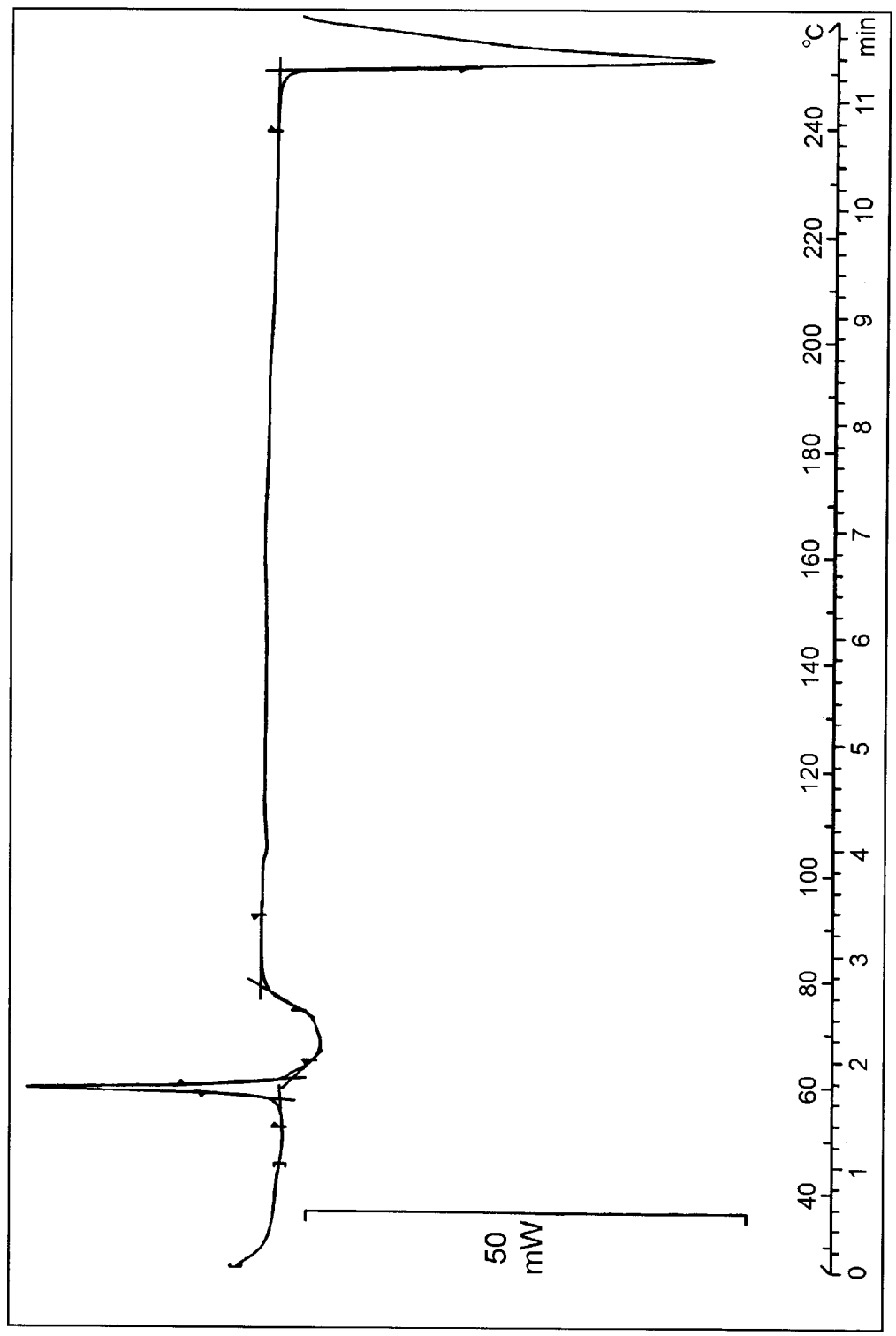
FIG. 12 is a drawing representing a DSC pattern of the amorphous compound obtained in Example 6.

DSC analysis was conducted under the following conditions, using approximately 3 mg each of the crystals obtained in Comparative Example 1, Comparative Example 3 and Example 4A (the crystal form A, the crystal form B(2) and the crystal form C). The DSC patterns of the respective crystals are shown in FIG. 10 and FIG. 11 (magnification of 40-230° C.). DSC analysis was conducted under the same conditions, using approximately 4 mg of the amorphous compound obtained in Example 6. The DSC pattern of the amorphous compound is shown in FIG. 12. The endothermic peaks and exothermic peaks are shown in Table 4.

Measuring apparatus: DSC822$^e$ by Mettler Toledo
Sample pan material: aluminum
Nitrogen gas flow (40 mL/min)
Start temperature: 25° C.
End temperature: 260° C.
Temperature elevating rate: 5° C./min

TABLE 4

| Crystal | Peak form, onset temperature |
|---|---|
| Crystal form A | Endothermic peak, about 248° C. |
| Crystal form B | Endothermic peak, about 92° C. |
|  | Exothermic peak, about 165° C. |
|  | Endothermic peak, about 248° C. |
| Crystal form B | Exothermic peak, about 154° C. |
|  | Endothermic peak, about 248° C. |
| Hydrate crystals | Exothermic peak, about 57° C. |
|  | Endothermic peak, about 249° C. |

For the crystal form A, no change in the powder X-ray diffraction pattern was seen from 30° C. to 250° C., but disappearance of crystallinity was observed at 260° C. The endothermic peak around 248° C. found by DSC analysis of the crystal form A was shown to have appeared due to melting of the crystals. These results indicated that the crystal form A undergoes no change in crystal form by heating in a range from ordinary temperature to its melting point of about 248° C.

For the crystal form B, a significant change in the powder X-ray diffraction pattern was observed between 90 and 100° C. A significant change in the powder X-ray diffraction pattern was also observed between 160 and 180° C., with disappearance of crystallinity being observed at 260° C. The endothermic peak around 92° C. and the exothermic peak around 165° C. found by DSC analysis were shown to have appeared due to these changes in the crystal form. The powder X-ray diffraction pattern also indicated a change to the same crystal form as the crystal form A at 180° C. and higher. These results indicated that the crystal form B transforms to another crystal form (B') at about 90° C., after which it transforms to the crystal form A at about 170° C. and melts at about 248° C. as the crystal form A.

For the crystal form C, a significant change in the powder X-ray diffraction pattern was observed between 160 and 190° C. The exothermic peak around 154° C. found by DSC analysis of the crystal form C was shown to have appeared due to change in the crystal form. The powder X-ray diffraction pattern also indicated a change to the same crystal as the crystal form A at 190° C. and higher. These results indicated that the crystal form C transforms to the crystal form A at about 170° C. and melts at about 248° C. as the crystal form A.

Figure 13:
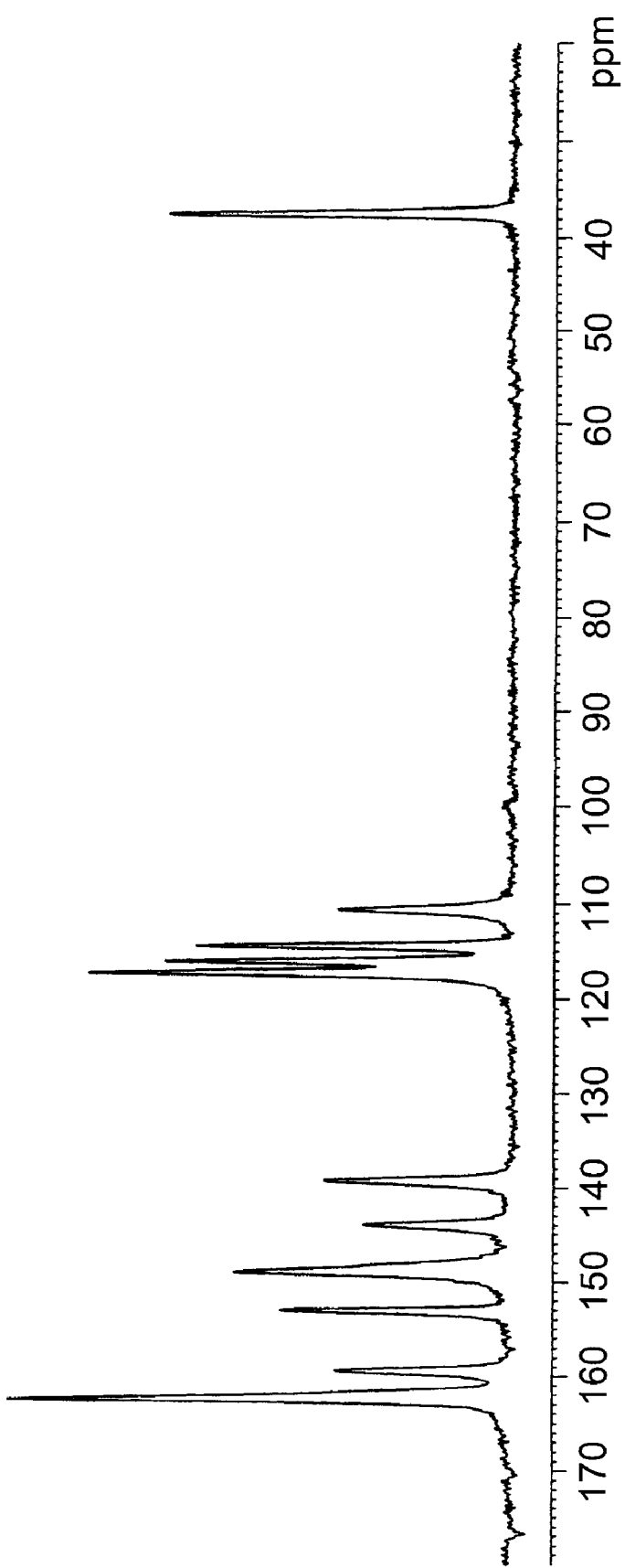
FIG. 13 is a drawing representing a $^{13}C$ solid state NMR spectrum of the crystals obtained in Comparative Example 3.
Figure 14:
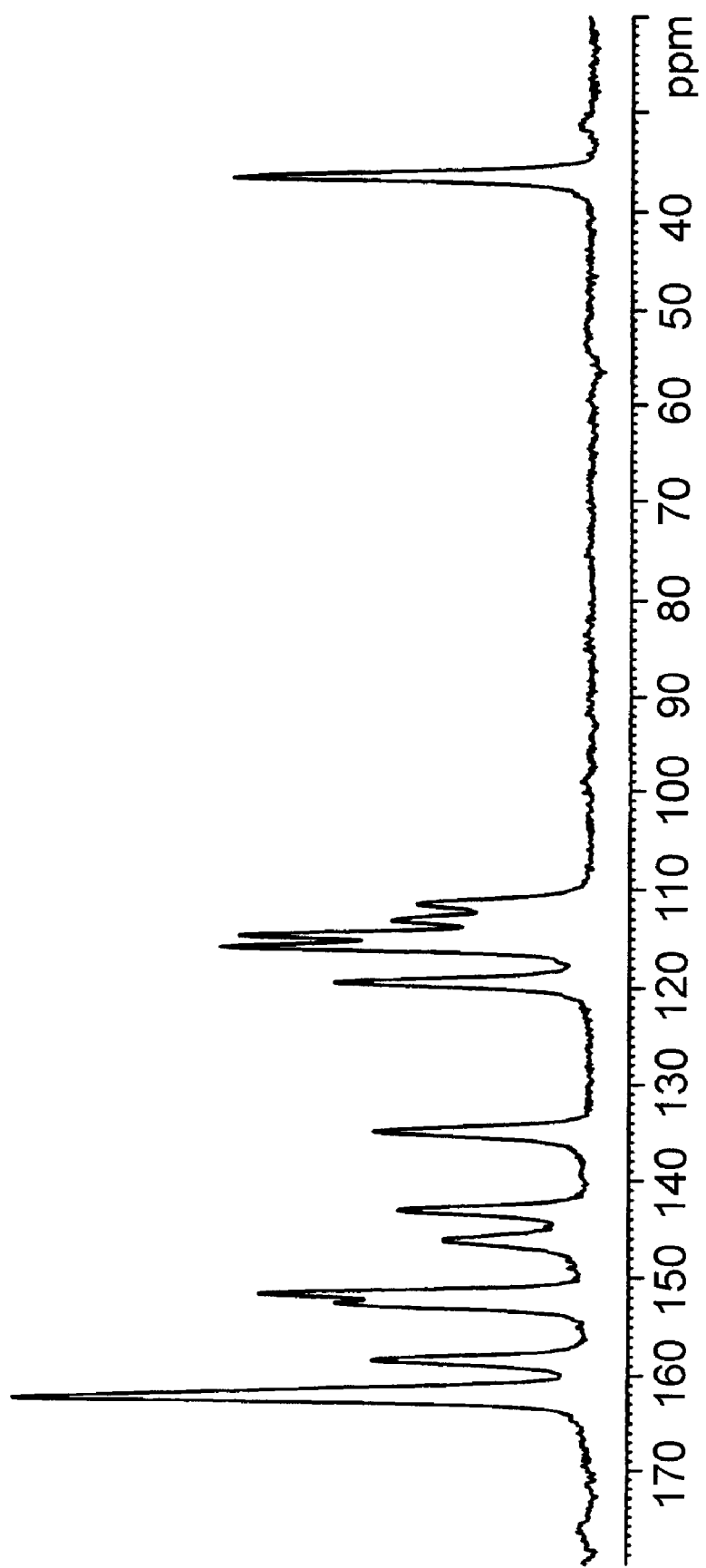
FIG. 14 is a drawing representing a $^{13}C$ solid state NMR spectrum of the crystals obtained in Example 4A.

Measurement of $^{13}$C Solid State NMR Spectrum $^{13}$C solid state NMR spectra for the respective crystals obtained in Comparative Example 3 and Example 4 (the crystal form B(2) and the crystal form C) were measured under the following conditions. The $^{13}$C solid state NMR spectra for the respective crystals are shown in FIG. 13 and FIG. 14. Table 5 shows chemical shifts for the respective crystals. Characteristic peaks in 110.6 ppm and 117.2 ppm were found for the crystal form B, whereas characteristic peaks in 134.9 ppm and 146.3 ppm were found for the crystal form C.

Measuring apparatus: AVANCE 400 MHz (Bruker)
Probe: 7 mm-CP/MAS (Bruker)
NMR cell diameter: 7 mm
Frequency of cell: 6000 round/sec
Measurement method: CPTOSS method
Latency: 10 sec
Contact time: 5000 microseconds
Accumulation: 1024 times
External standard: setting the chemical shift of carbonyl carbon of glycine as 176.03 ppm

TABLE 5

| Crystal form B | Crystal form C |
|---|---|
| 162.5 | 162.4 |
| 159.4 | 158.5 |
| 153.1 | 152.6 |
| 149.0 | 151.7 |
| 144.0 | 146.3 |
| 139.3 | 143.1 |
| 117.2 | 134.9 |
| 116.0 | 119.4 |
| 114.4 | 115.9 |
| 110.6 | 114.7 |
| 37.4 | 113.2 |
|  | 111.5 |
|  | 36.4 |

Unit: ppm

Measurement of Infrared Absorption Spectrum

Figure 15:
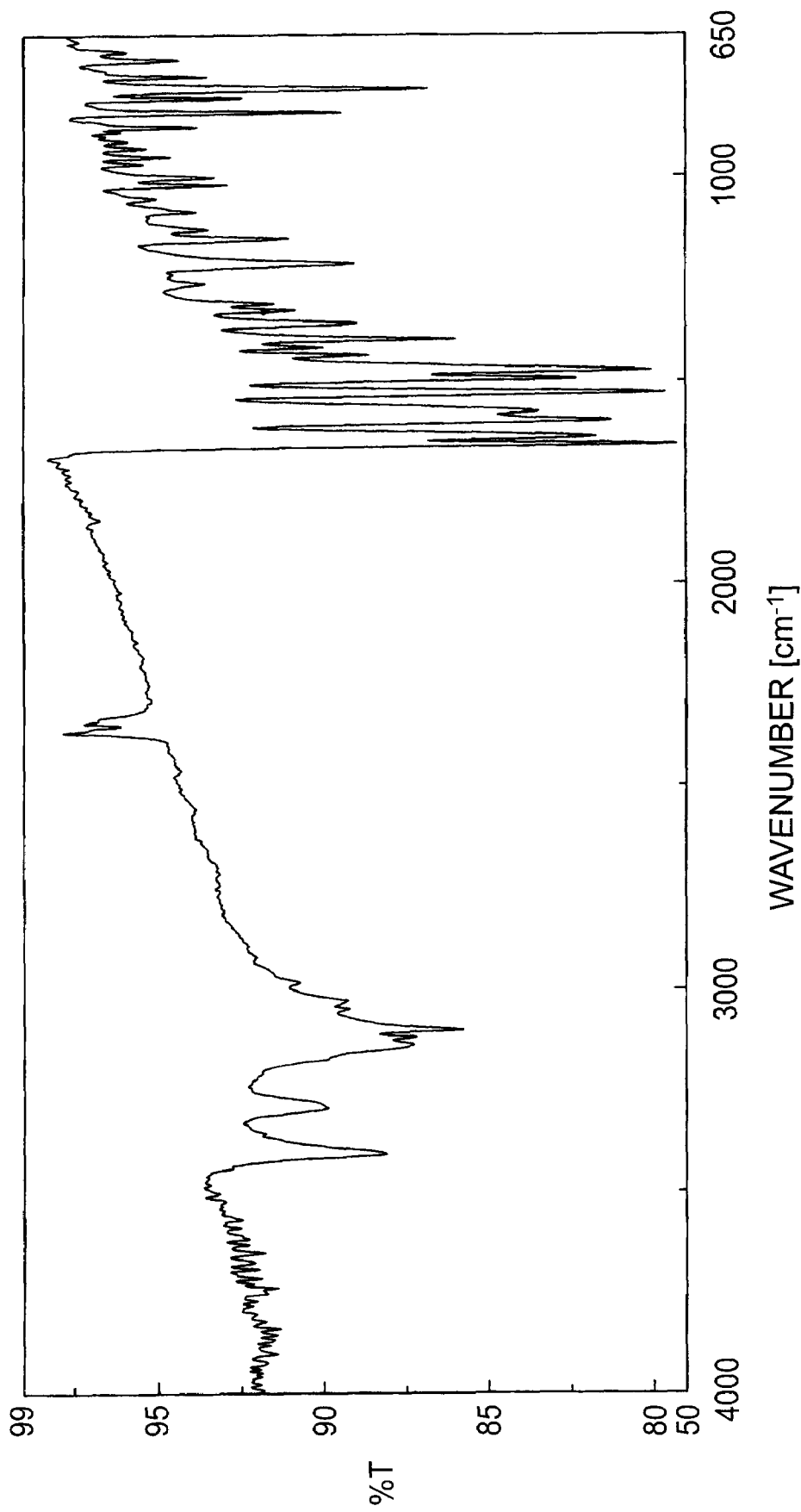
FIG. 15 is a drawing representing an infrared absorption spectrum of the crystals obtained in Comparative Example 3.

Infrared absorption spectra for the respective crystals obtained in Comparative Example 3 and Example 4A (the crystal form B(2) and the crystal form C) were measured under the following conditions. The infrared absorption spectra for the respective crystals are shown in FIG. 15 and FIG. 16. Table 6 shows wavenumber (cm$^{-1}$) of absorption peaks for the respective crystals.
Measuring apparatus: FT/IR-620 (Jasco)
Measurement method: ATR method
Measuring range: 4000 cm$^{-1}$ to 650 cm$^{-1}$
Resolution: 4 cm$^{-1}$

TABLE 6

| Crystal form B | | Crystal form C | |
|---|---|---|---|
| 3410 | 1156 | 3464 | 1077 |
| 3300 | 1022 | 3146 | 1016 |
| 3102 | 1004 | 1671 | 884 |
| 1658 | 950 | 1644 | 857 |
| 1638 | 875 | 1603 | 802 |
| 1598 | 838 | 1568 | 744 |
| 1529 | 803 | 1523 | 712 |
| 1495 | 781 | 1490 | 693 |
| 1474 | 750 | 1470 | |
| 1436 | 709 | 1407 | |
| 1397 | | 1355 | |
| 1359 | | 1326 | |
| 1329 | | 1208 | |
| 1217 | | 1176 | |

Unit: cm$^{-1}$

Test Example 1

Solubility

Approximately 50 mg each of the crystals and amorphous compound obtained in Comparative Example 3, Example 4A, Example 5 and Example 6 (the crystal form B(2), the crystal form C, the hydrate crystals and the amorphous compound) was used for evaluation of solubility in Disintegration Test, the 2nd fluid described in the Japanese pharmacopoeia, 14th Edition. First, 500 mL of the 2nd fluid was stirred at 50 rpm with paddles (Toyama Co., Ltd.; DISSOLUTION TESTER), then after the crystals and amorphous compound were added, the solution was sampled at each time period. The sampled solutions were filtered through a filter (0.2 μm), and the concentration of 5-[2-amino-4-(2-furyl)pyrimidin-5-yl]-1-methylpyridin-2(1H)-one in the solution was measured by HPLC method. The conditions for HPLC method are shown below. The obtained results were show in FIG. 17.

(HPLC conditions)
Column: CAPCELL PAK C18 AQ, S-5 μm, 4.6 mm ID×250 mm length (Shiseido, Japan)
Column temperature: a constant temperature around 30° C.
Detection wavelength: 262 nm
Flow rate: 1.0 mL/min
Mobile phase:
Solution A: acetonitrile/water/1M ammonium acetate (10:1000:1, v/v/v)
Solution B: acetonitrile/water/1M ammonium acetate (900:100:1, v/v/v)

TABLE 7

| Gradient: | |
|---|---|
| Time (min) | (B) conc. (%) |
| 0 | 10 |
| 20 | 10 |
| 40 | 100 |
| 50 | 100 |
| 50.1 | 10 |
| 70 | Stop |

Figure 17:
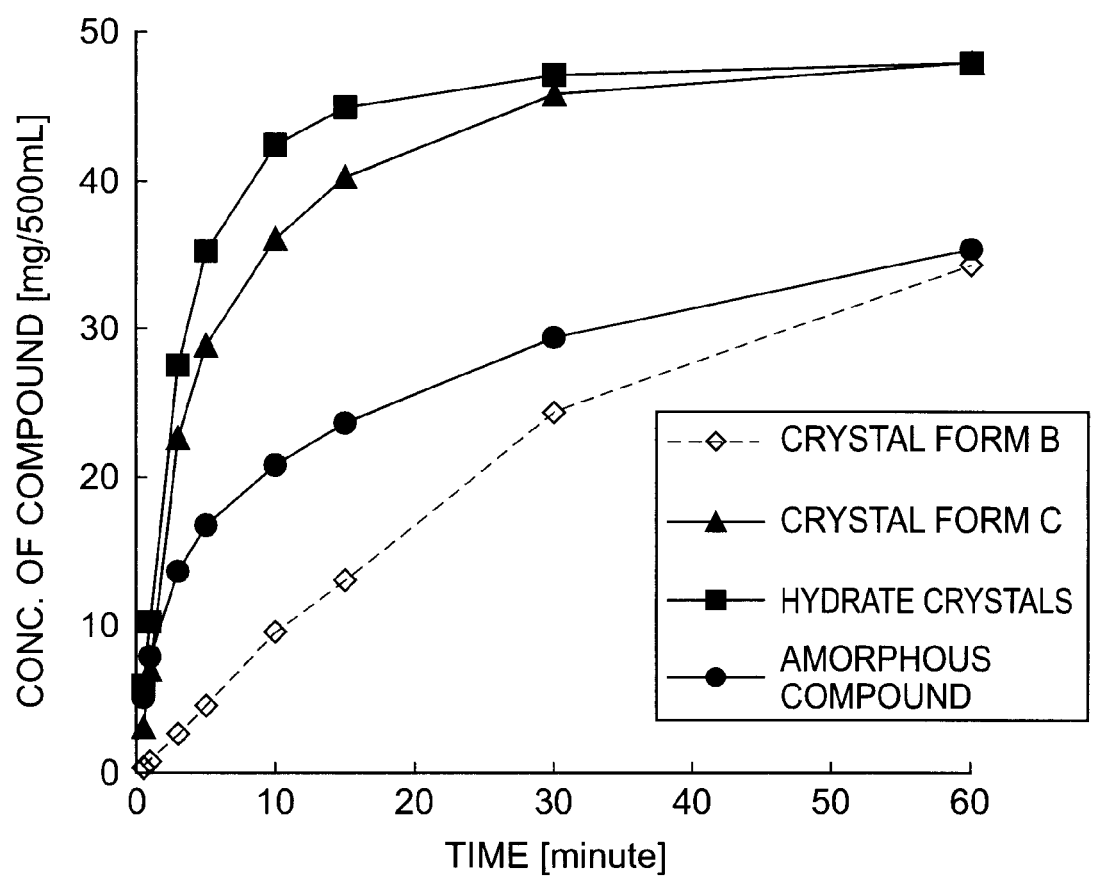
FIG. 17 is a graph showing the results in Test Example 1.

As shown in FIG. 17, it is clear that the crystal form C, the hydrate crystals and the amorphous compound are superior in solubility than the crystal form B.

INDUSTRIAL APPLICABILITY

The present invention provides crystals of 5-[2-amino-4-(2-furyl)pyrimidin-5-yl]-1-methylpyridin-2(1H)-one (crystal form C) which consist of a homogenous crystal form and are excellent in solubility and a process for preparing the same. The present invention provides also crystals of 5-[2-amino-4-(2-furyl)pyrimidin-5-yl]-1-methylpyridin-2(1H)-one hydrate which consist of a homogenous crystal form and are excellent in solubility and a process for preparing the same. The present invention provides also amorphous 5-[2-amino-4-(2-furyl)pyrimidin-5-yl]-1-methylpyridin-2(1H)-one which is excellent in solubility and a process for preparing the same. These crystals and amorphous compound are suitable for using as an active ingredient of a pharmaceutical composition, particularly a therapeutic agent for constipation.

Furthermore, the present invention provides a process for preparing 5-[2-amino-4-(2-furyl)pyrimidin-5-yl]-1-methylpyridin-2(1H)-one, which has less steps and amount of alkyl halides used. The preparing process is industrially advantageous.

What is claimed is:

1. A process for preparing a compound (I), a salt or a hydrate of the foregoing

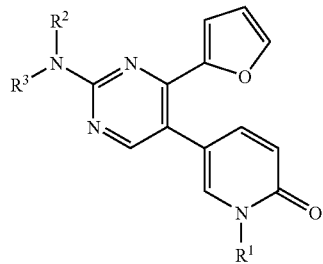

(I)

wherein $R^1$ represents C1-6 alkyl and $R^2$ and $R^3$ independently represent hydrogen or C1-6 alkyl, by allowing a compound (II)

(II)

[structure of compound II]

wherein $R^1$ is as defined above, to react with a compound (III)

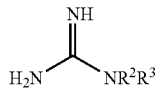

(III)

wherein $R^2$ and $R^3$ are as defined above.

2. A process according to claim 1, wherein $R^1$ is methyl.

3. A process according to any one of claims 1 or 2, wherein $R^2$ and $R^3$ are hydrogen.

* * * * *